(12) United States Patent
Old et al.

(10) Patent No.: US 7,592,364 B2
(45) Date of Patent: Sep. 22, 2009

(54) SUBSTITUTED GAMMA LACTAMS AS THERAPEUTIC AGENTS

(75) Inventors: David W. Old, Irvine, CA (US); Danny T. Dinh, Garden Grove, CA (US)

(73) Assignee: Allergan, Inc., Irvine, CA (US)

( * ) Notice: Subject to any disclaimer, the term of this patent is extended or adjusted under 35 U.S.C. 154(b) by 227 days.

(21) Appl. No.: 11/672,433

(22) Filed: Feb. 7, 2007

(65) Prior Publication Data

US 2007/0203222 A1    Aug. 30, 2007

Related U.S. Application Data

(60) Provisional application No. 60/777,506, filed on Feb. 28, 2006.

(51) Int. Cl.
*A61K 31/4015*  (2006.01)
*C07D 409/06*  (2006.01)
*C07D 409/12*  (2006.01)
*C07D 207/04*  (2006.01)

(52) U.S. Cl. ........................ 514/422; 514/424; 548/527; 548/551

(58) Field of Classification Search ................. 514/422, 514/424; 548/527, 537, 551
See application file for complete search history.

(56) References Cited

U.S. PATENT DOCUMENTS

| 6,437,146 | B1 | 8/2002 | Hattori et al. | |
|---|---|---|---|---|
| 6,573,294 | B1 | 6/2003 | Old et al. | |
| 6,710,072 | B2 | 3/2004 | Burk et al. | |
| 2003/0120079 | A1 | 6/2003 | Elworthy et al. | |
| 2006/0205800 | A1* | 9/2006 | Donde et al. | 514/381 |
| 2007/0219265 | A1* | 9/2007 | Old et al. | 514/422 |
| 2007/0265330 | A1* | 11/2007 | Old et al. | 514/422 |
| 2007/0287742 | A1* | 12/2007 | Old et al. | 514/424 |
| 2008/0039505 | A1* | 2/2008 | Old et al. | 514/342 |
| 2008/0269498 | A1* | 10/2008 | Old | 548/188 |

FOREIGN PATENT DOCUMENTS

| WO | 03/103604 | 12/2003 |
|---|---|---|
| WO | WO 2004/037813 | 5/2004 |

OTHER PUBLICATIONS

Mandred E. Wolff, Burger's Medicinal Chemistry and Drug Discovery, 1995, ImmunoPharmaceutics, Inc., Fifth Edition, vol. I: Principles and Practice, pp. 975-977.*

* cited by examiner

*Primary Examiner*—Kamal A Saeed
*Assistant Examiner*—Kristin Bianchi
(74) *Attorney, Agent, or Firm*—Kevin J. Forrestal; Allergan, Inc.

(57) ABSTRACT

Therapeutic compounds, compositions, medicaments, and methods are disclosed herein.

20 Claims, 12 Drawing Sheets

Fig. 12

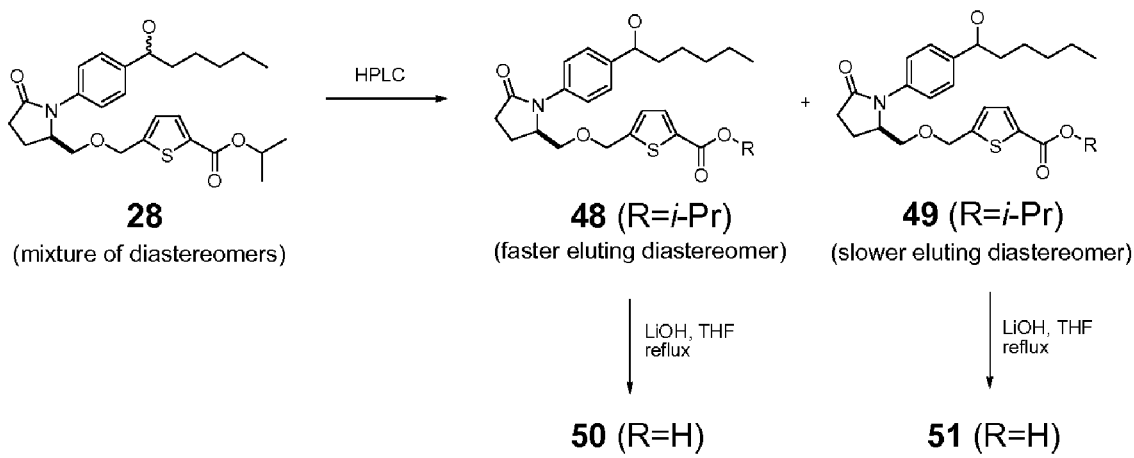

Figure 1:
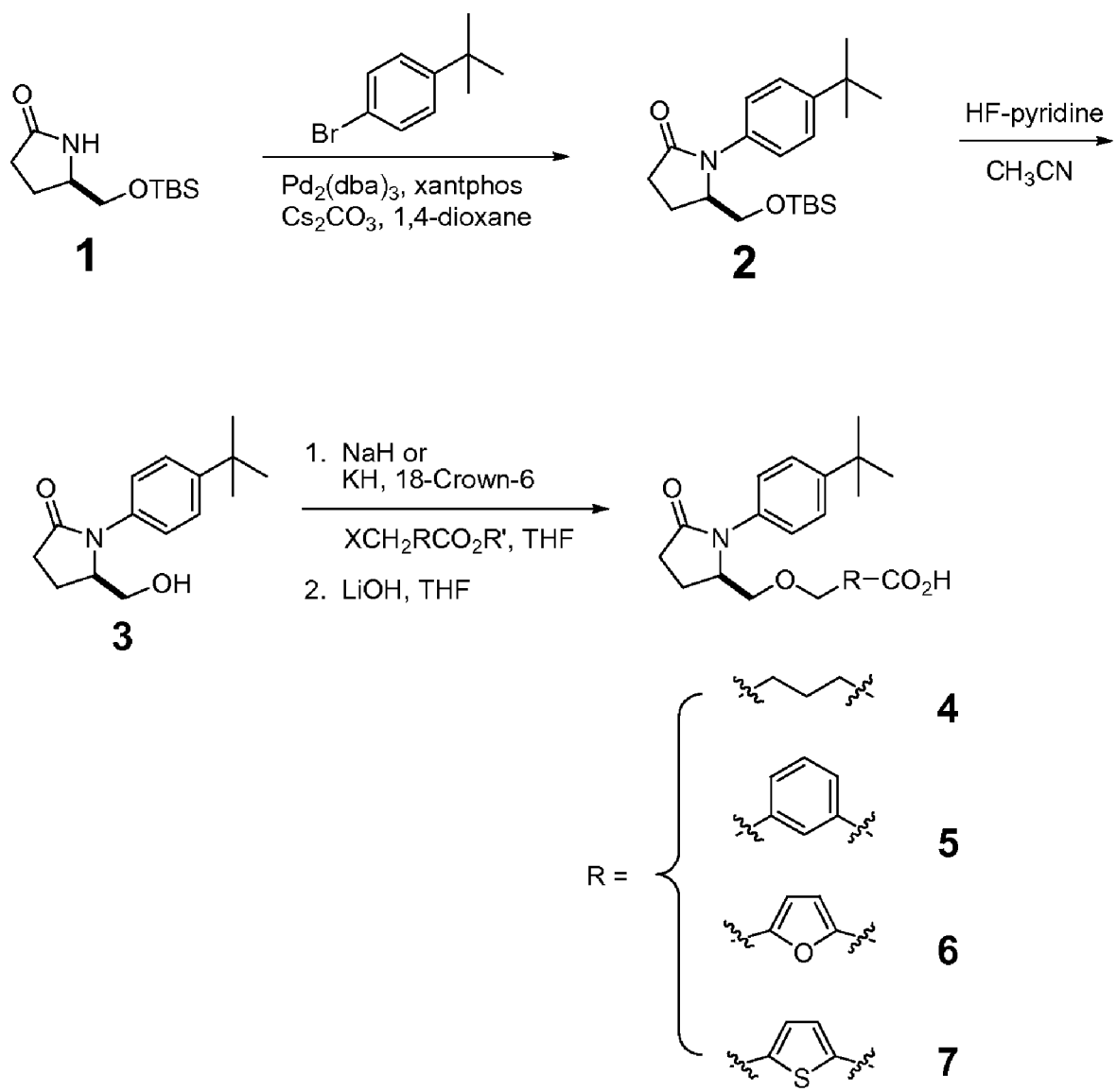

28
(mixture of diastereomers)

→ HPLC →

48 (R=*i*-Pr)
(faster eluting diastereomer)

+

49 (R=*i*-Pr)
(slower eluting diastereomer)

↓ LiOH, THF reflux

↓ LiOH, THF reflux

50 (R=H)

51 (R=H)

Fig. 13

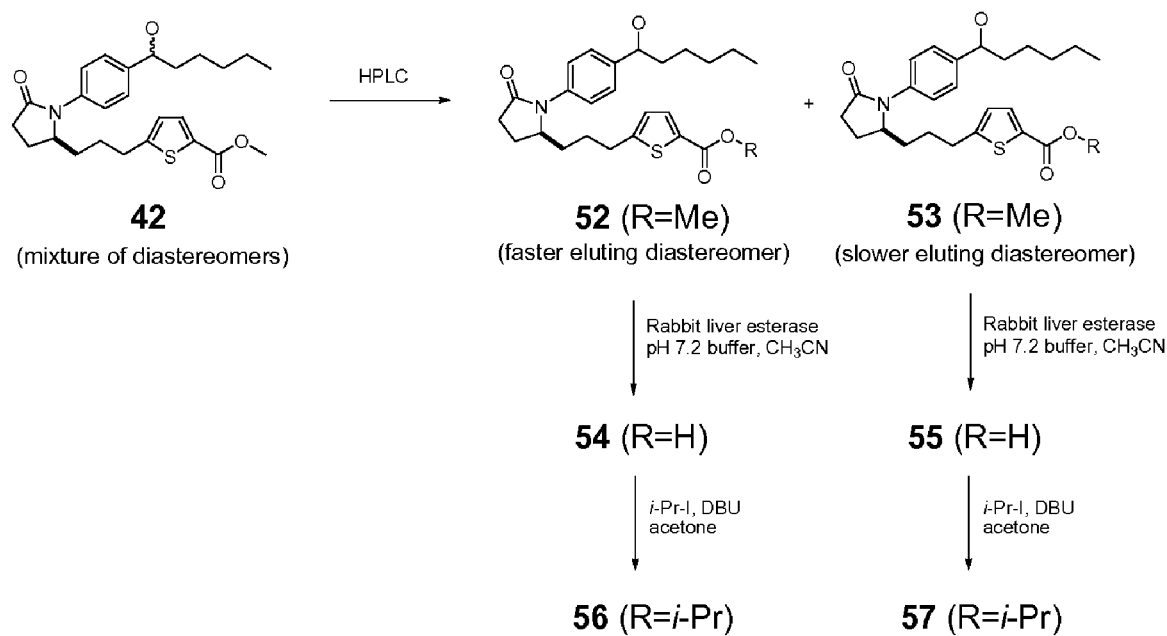

42
(mixture of diastereomers)

→ HPLC →

52 (R=Me)
(faster eluting diastereomer)

+

53 (R=Me)
(slower eluting diastereomer)

↓ Rabbit liver esterase
pH 7.2 buffer, CH$_3$CN

↓ Rabbit liver esterase
pH 7.2 buffer, CH$_3$CN

54 (R=H)

55 (R=H)

↓ *i*-Pr-I, DBU
acetone

↓ *i*-Pr-I, DBU
acetone

56 (R=*i*-Pr)

57 (R=*i*-Pr)

SUBSTITUTED GAMMA LACTAMS AS THERAPEUTIC AGENTS

CROSS-REFERENCE TO RELATED APPLICATION

This application is based, and claims priority under 35 U.S.C. § 120 to U.S. Provisional Patent Application No. 60/777,506 filed on Feb. 28, 2006, and which is incorporated herein by reference.

BRIEF DESCRIPTION OF THE DRAWING FIGURES

Figure 2:
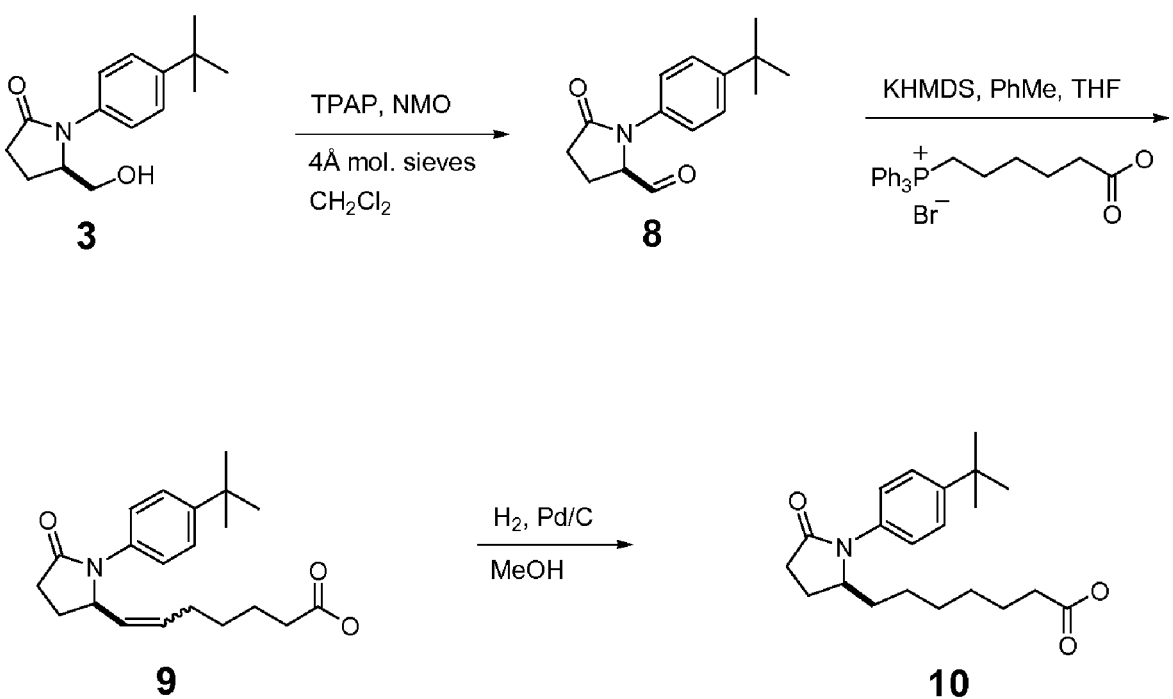
Figure 3:
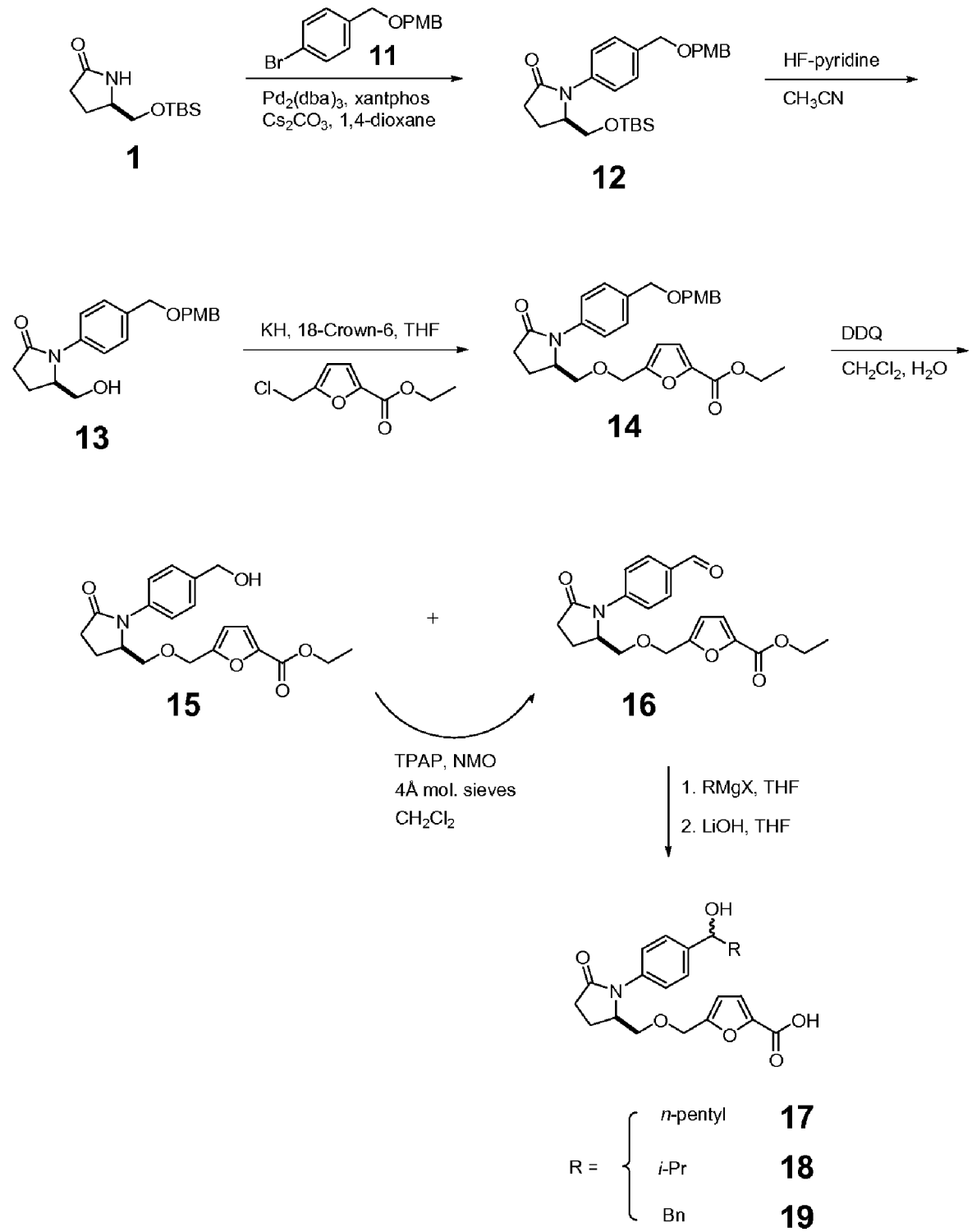
Figure 4:
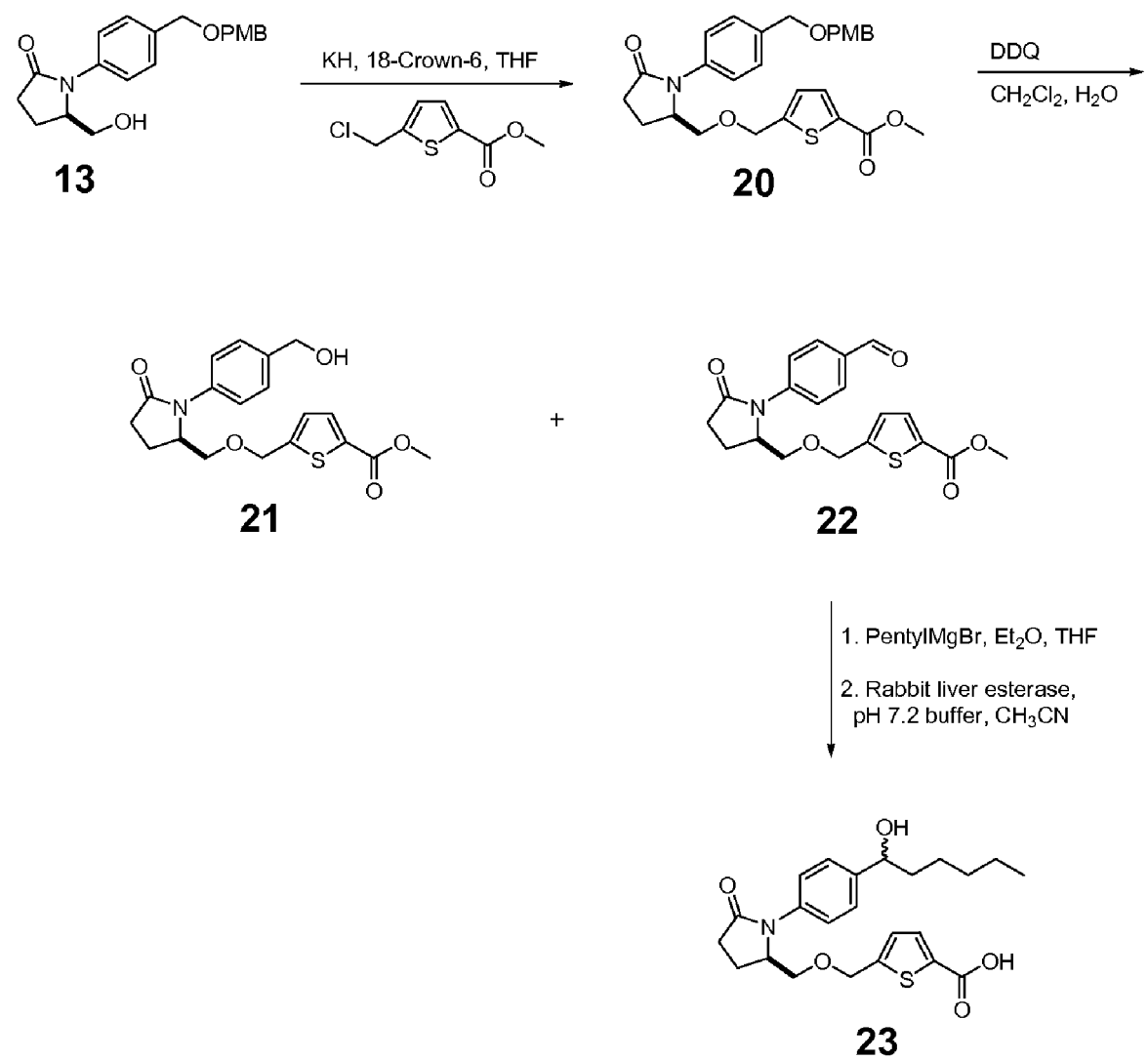
Figure 5:
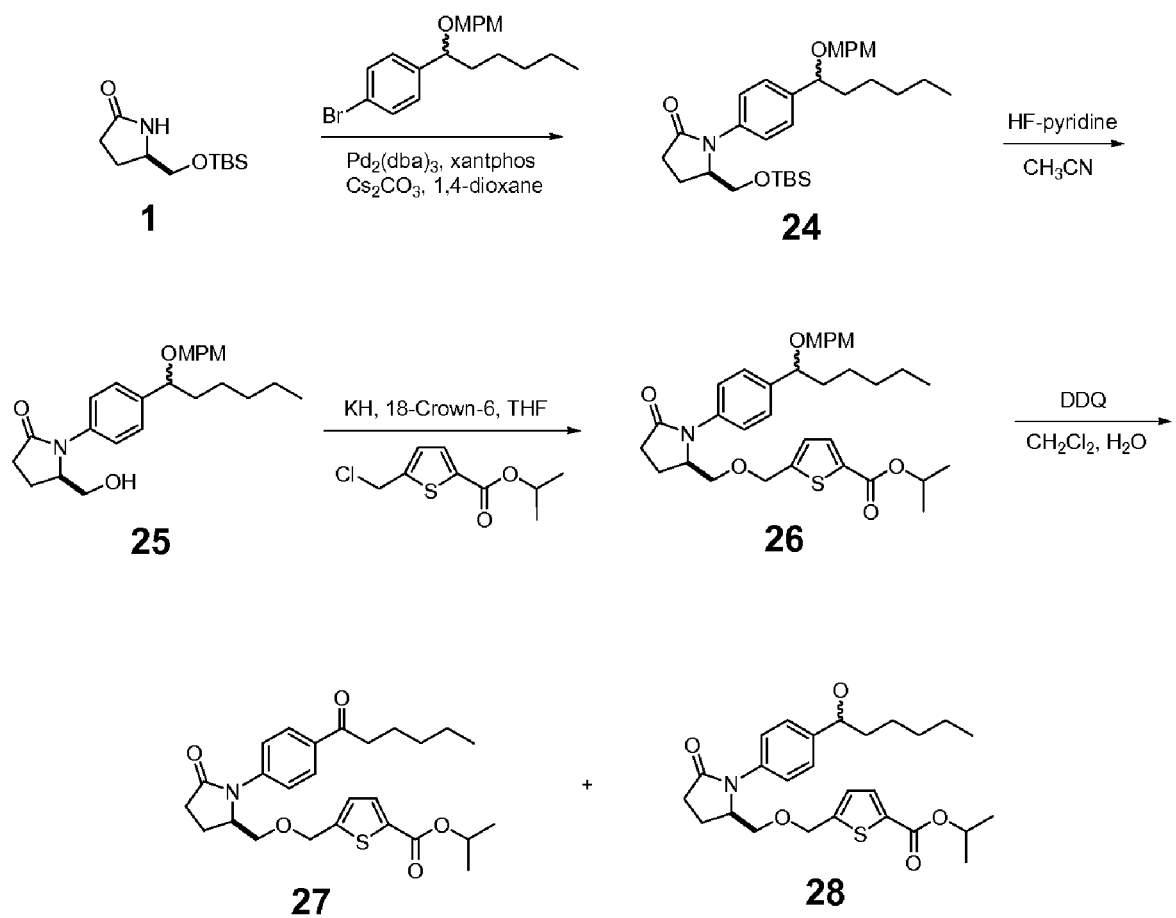
Figure 6:
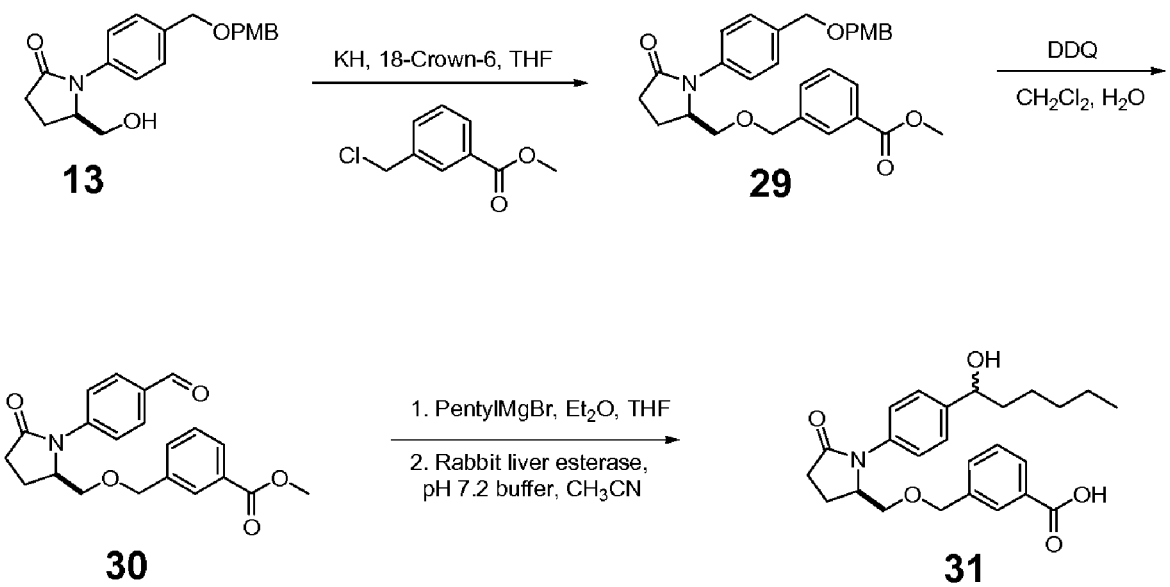
Figure 7:
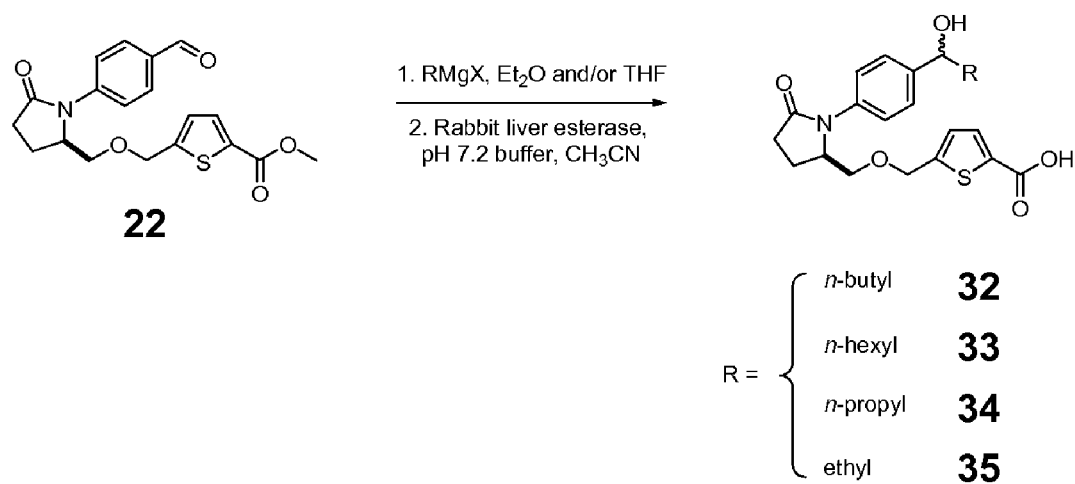
Figure 8:
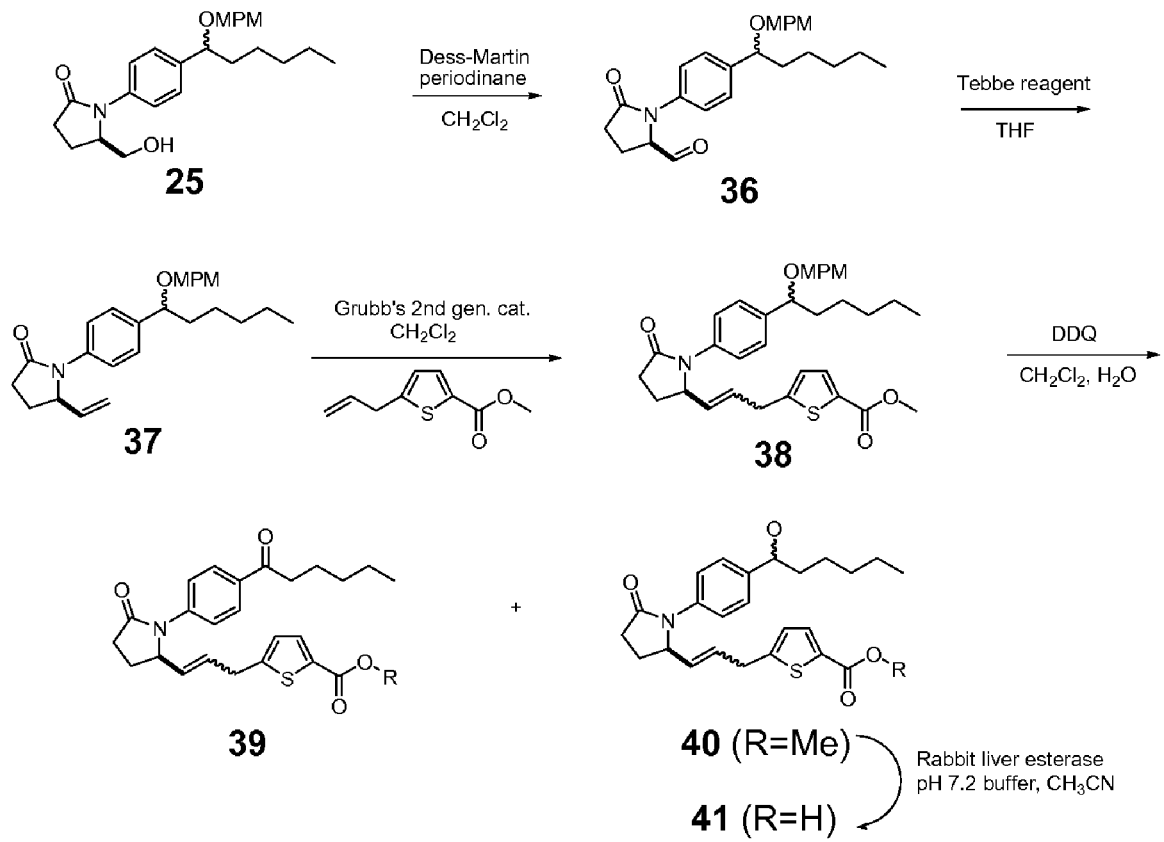
Figure 9:
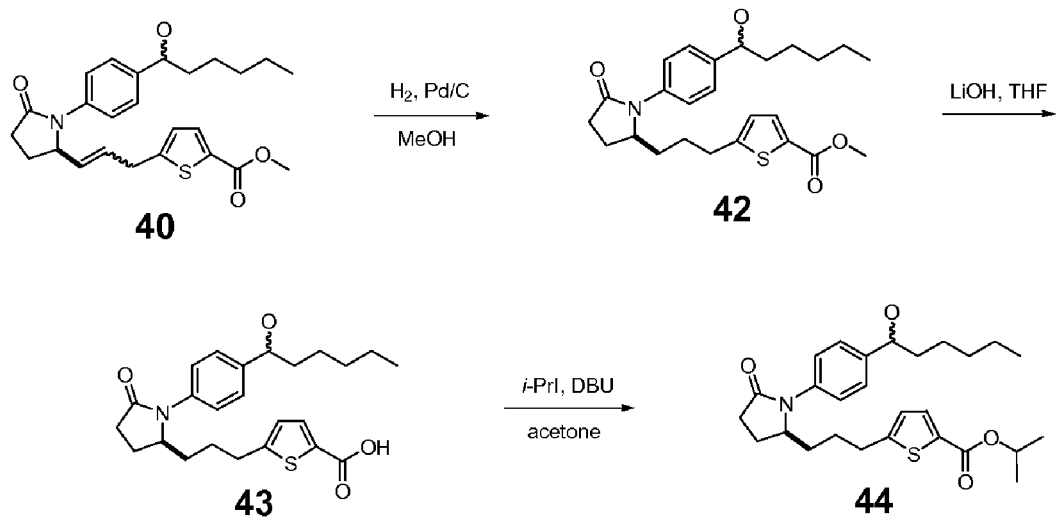
Figure 10:
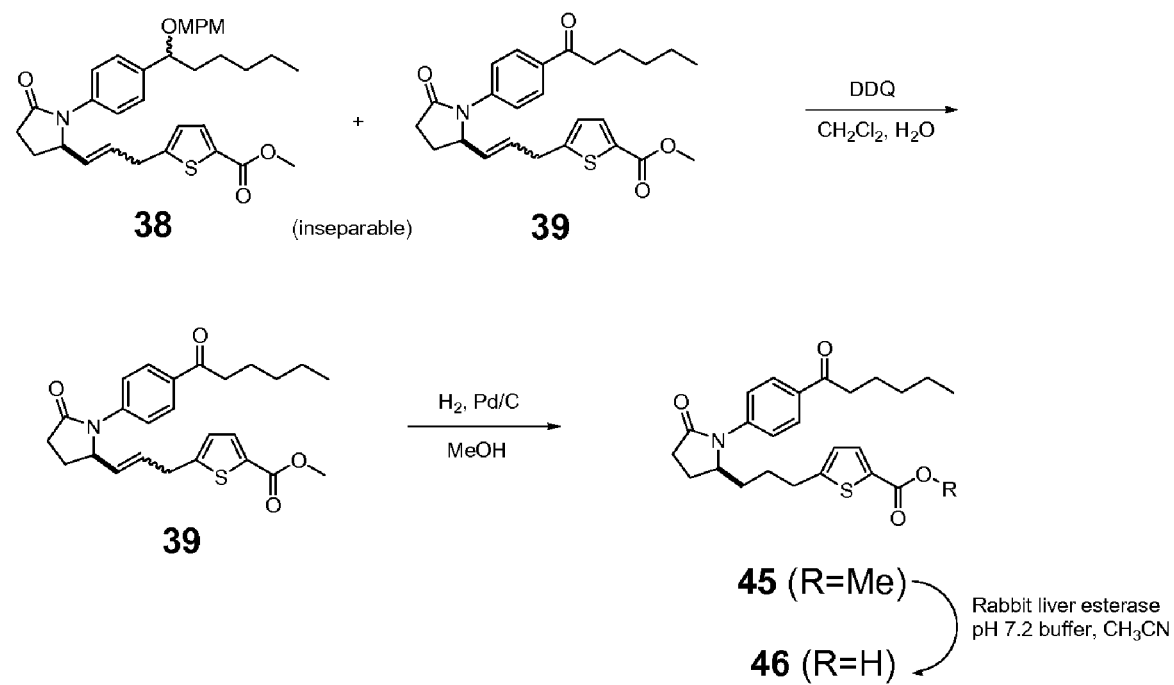
Figure 11:
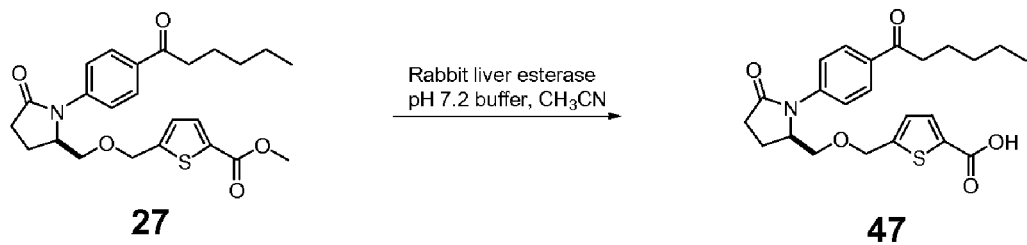
Figure 14:
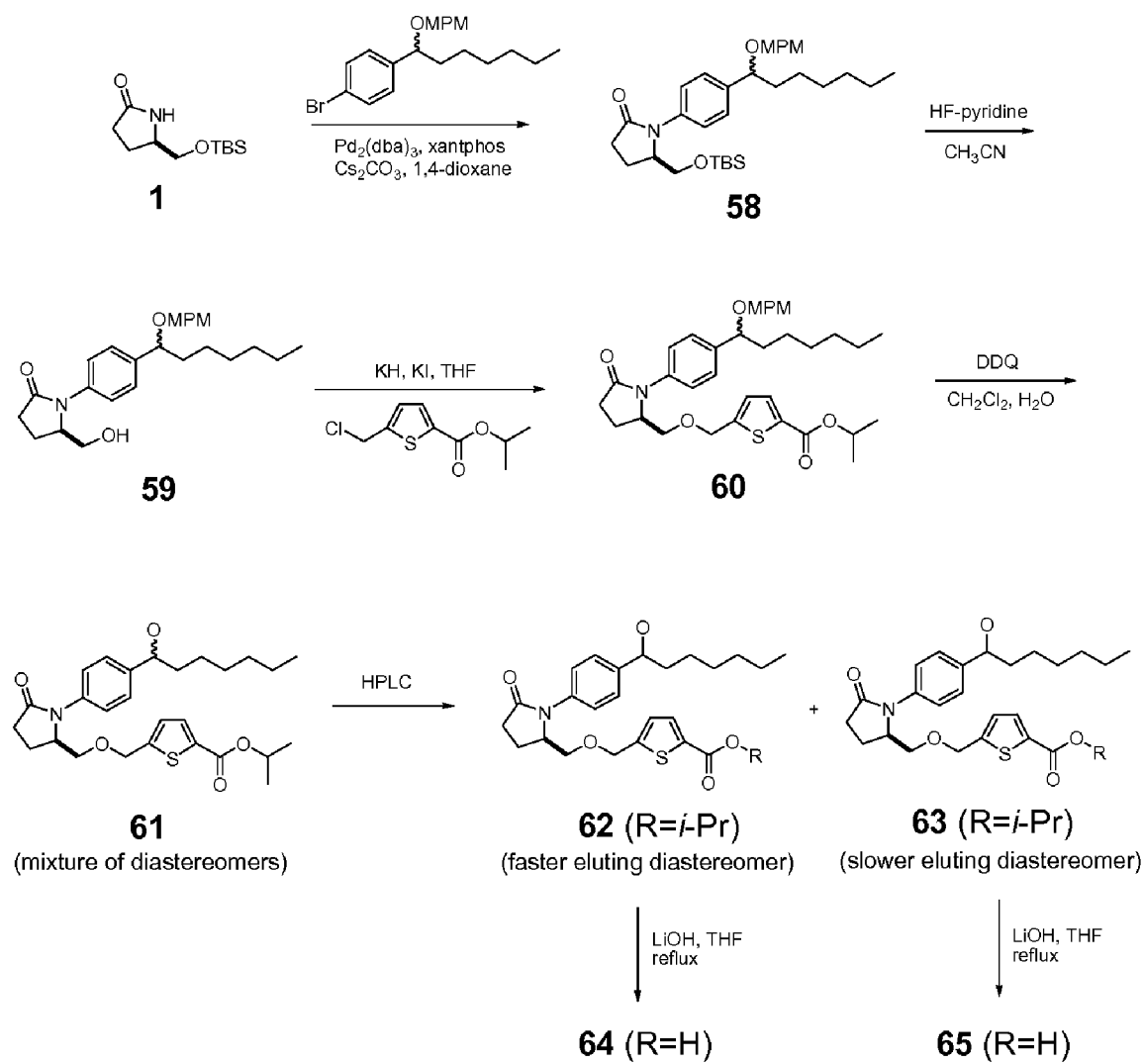
Figure 15:
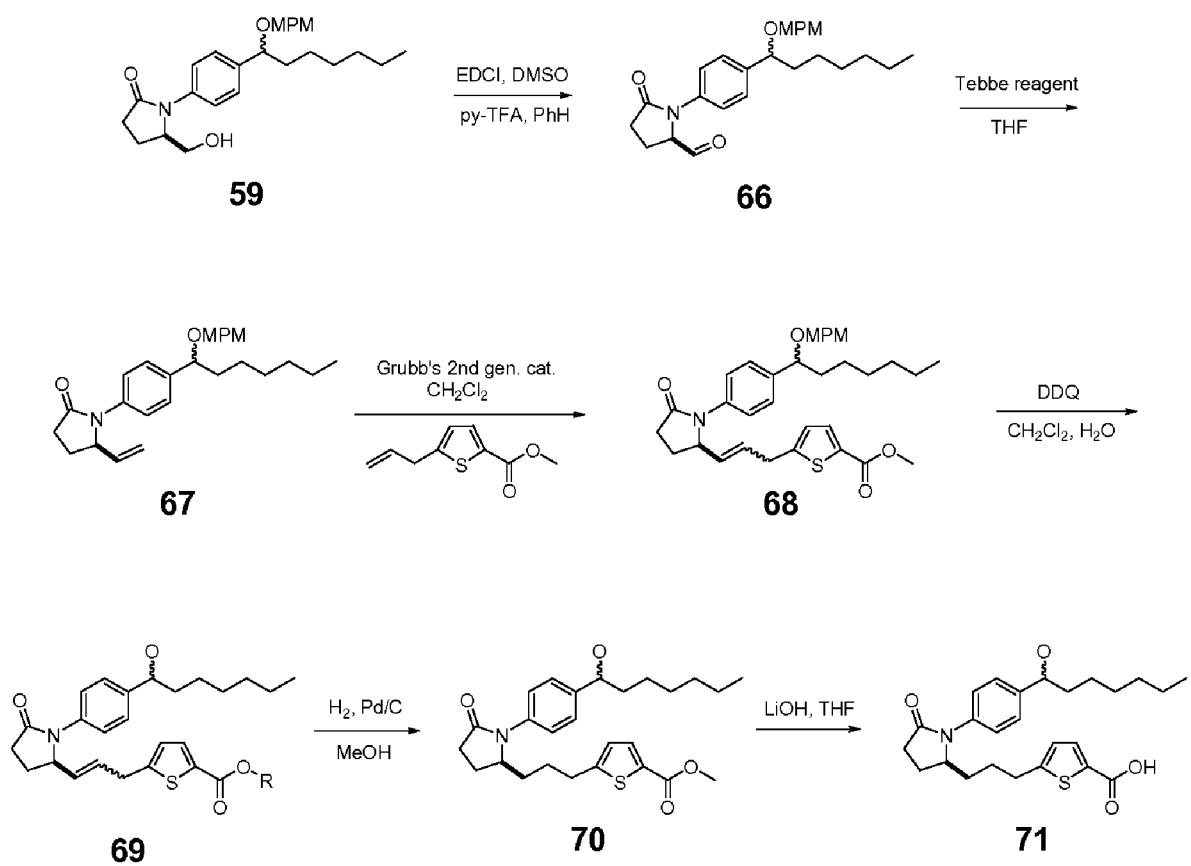
Figure 16:
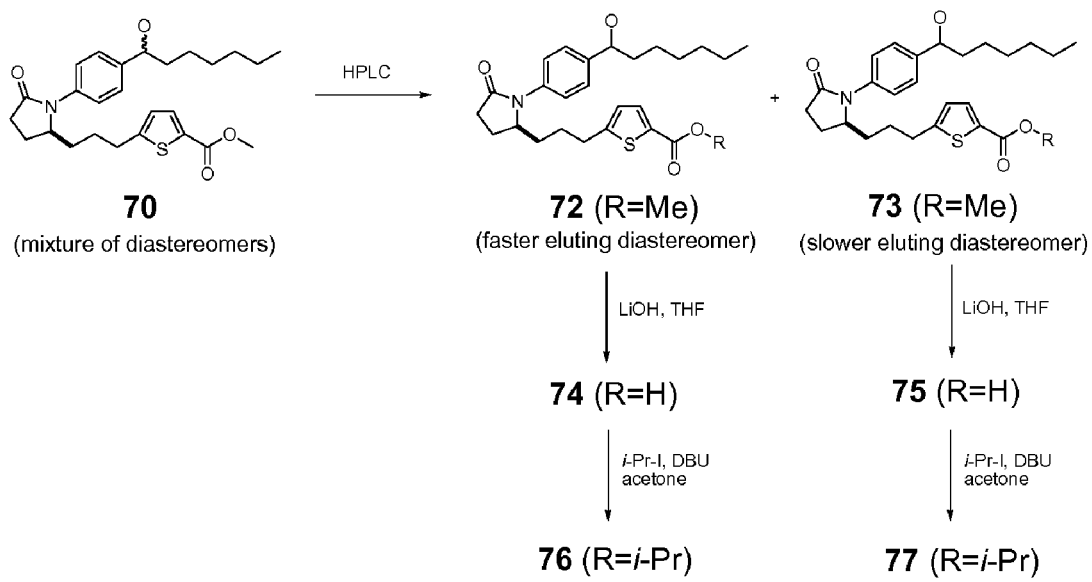
Figure 17:
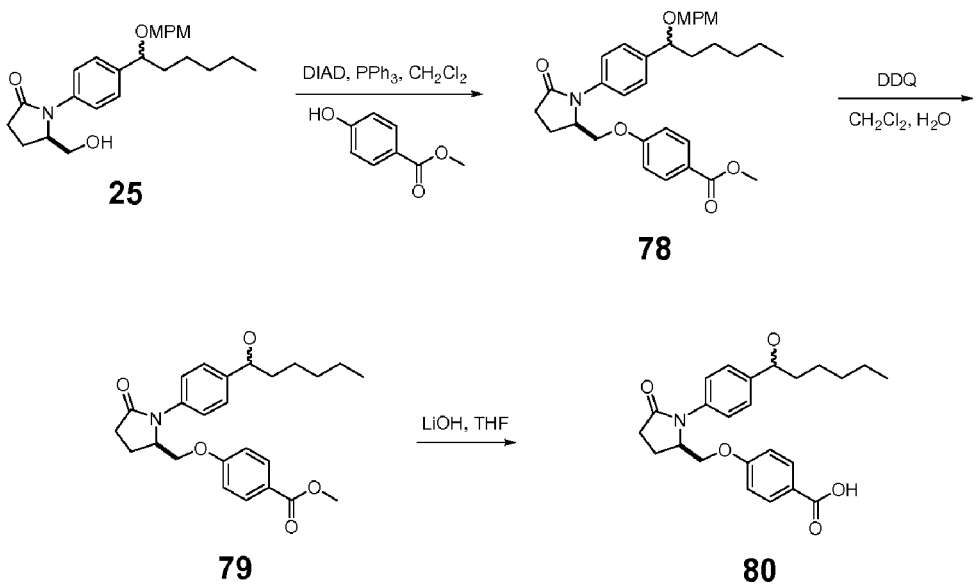

FIGS. 1-17 show examples of methods that can be used to prepare the compounds disclosed herein.

DESCRIPTION OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

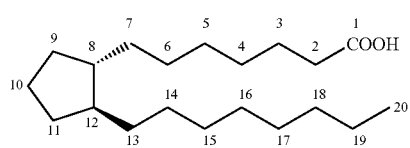

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

One embodiment is a compound according to the formula

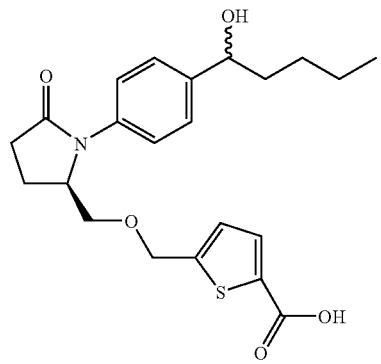

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

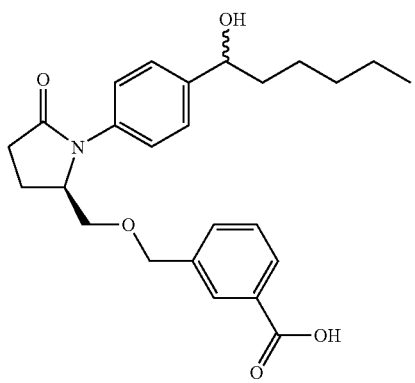

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

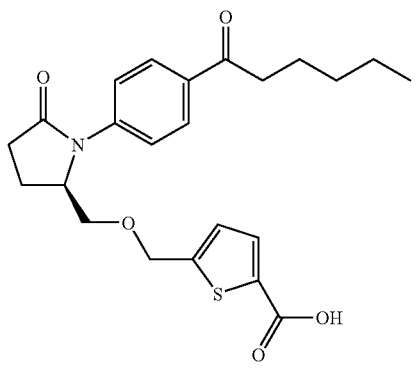

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

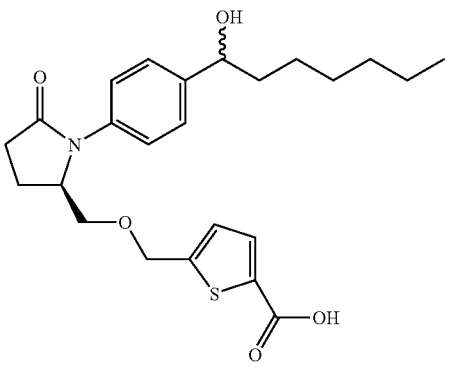

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

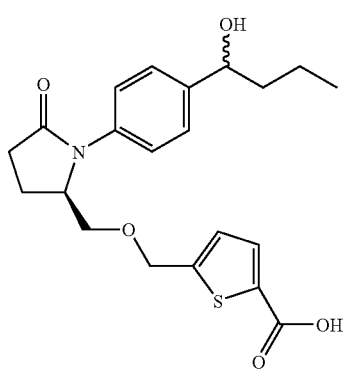

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

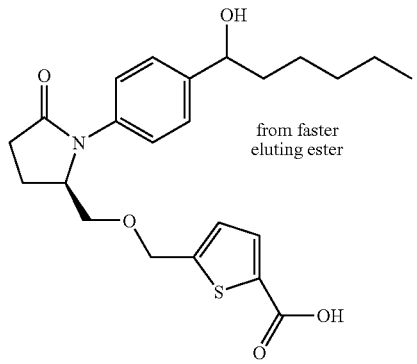

from faster eluting ester or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

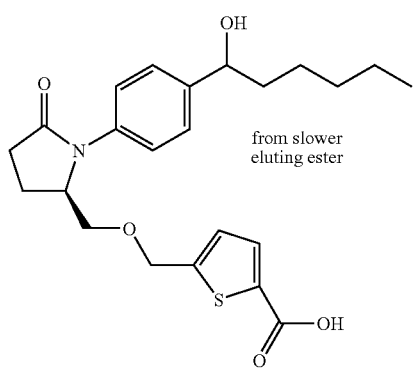

from slower eluting ester or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

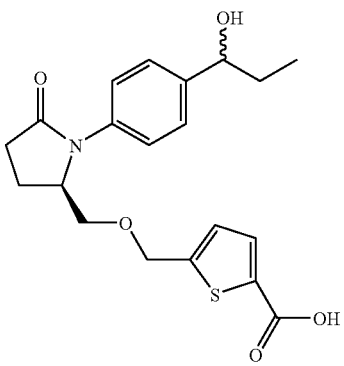

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

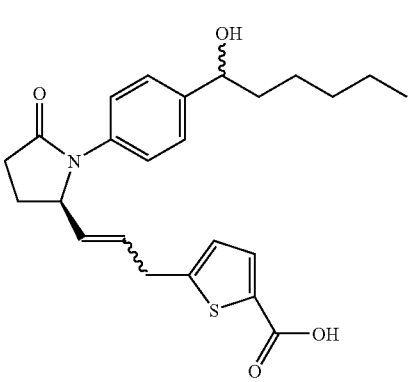

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formla

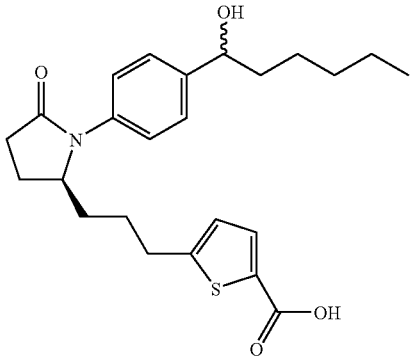

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

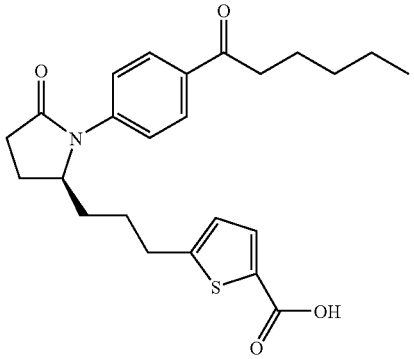

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

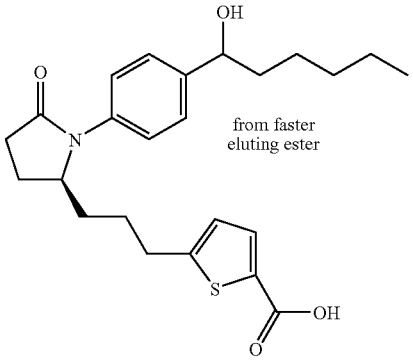

from faster eluting ester or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

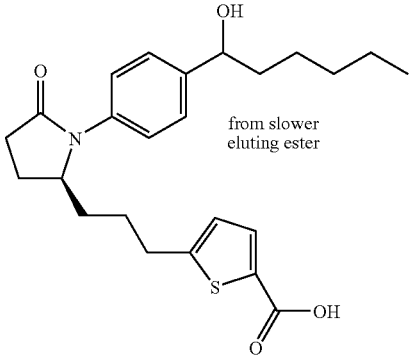

from slower eluting ester or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

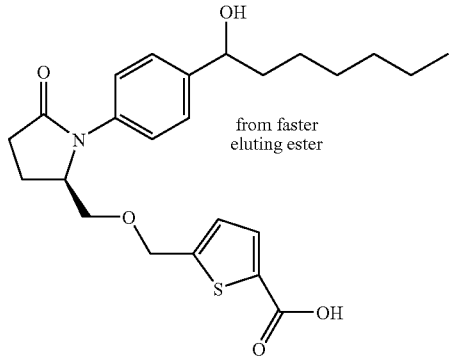

from faster eluting ester or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

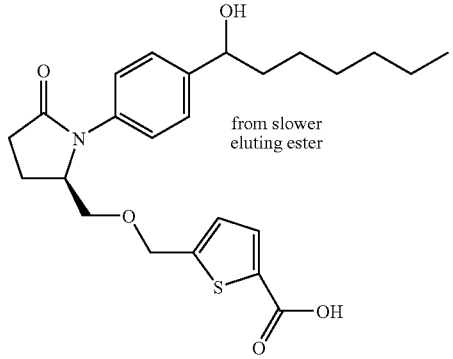

from slower eluting ester or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formla

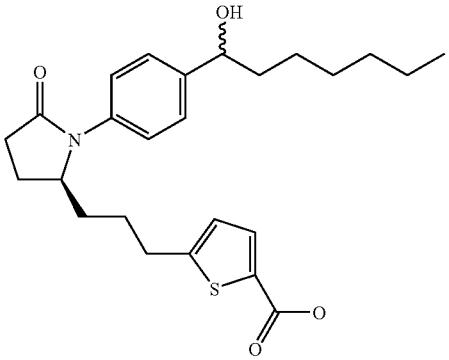

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

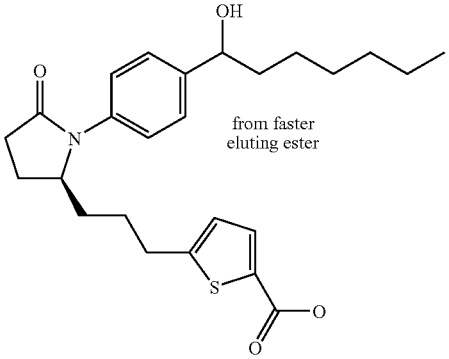

from faster eluting ester or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

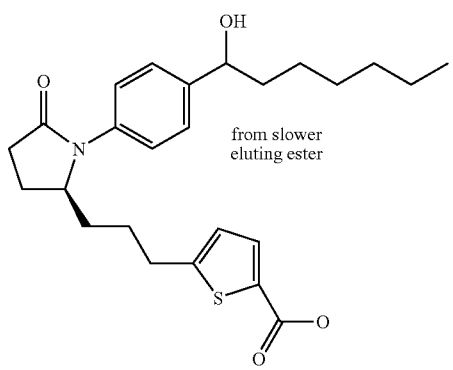

from slower eluting ester or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

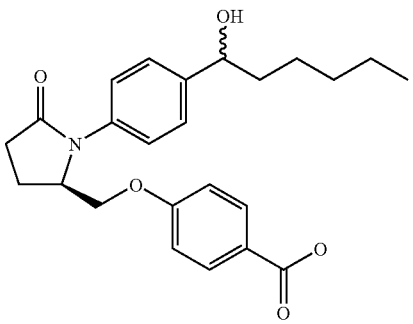

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

The compounds disclosed herein are useful for the prevention or treatment of glaucoma or ocular hypertension in mammals, or for the manufacture of a medicament for the treatment of glaucoma or ocular hypertension. They are also useful for the treatment of those diseases disclosed in the art as being amenable to treatment by prostaglandin $EP_2$ agonist, such as the ones listed previously.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

A metabolite is broadly defined as a compound which is formed in vivo from the disclosed compound.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |

| Ingredient | Amount (% w/v) |
| --- | --- |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

The compounds disclosed herein are also useful in combination with other drugs useful for the treatment of glaucoma or other conditions.

EXAMPLE 1

5-[(R)-1-(4-tert-Butyl-phenyl)-5-oxo-pyrrolidin-2-ylmethoxy]-pentanoic acid (4)

Step 1. Arylation of 1 to Give 2

A solution of amide 1 (3.30 g, 14.4 mmol) in 1,4-dioxane (25 mL) was added to a mixture of 4,5-bis(triphenylphosphino)-9,9-dimethylxanthene (xantphos, 600 mg, 1.04 mmol), $Pd_2(dba)_3$ (317 mg, 0.35 mmol) and $Cs_2CO_3$ (6.46 g, 19.8 mmol). 1-Bromo-4-tert-butylbenzene (2.40 mL, 13.8 mmol) was added and the reaction mixture was purged with nitrogen. The mixture was heated at reflux for 19 h, then cooled to rt. The reaction mixture was then filtered through celite, washing with $CH_2Cl_2$, and the filtrate was concentrated in vacuo. Purification of the residue by flash column chromatography on silica gel (10%→20% EtOAc/Hexane, gradient) afforded 3.53 g (71%) of the desired product 2.

Step 2. Deprotection of 2 to Give 3

HF-pyridine (5 mL) was added to a solution of silyl ether 2 (3.53 g, 9.76 mmol) in MeCN (20 mL) in a plastic bottle. The reaction was stirred at rt for 5 h, then was quenched with saturated aqueous $NaHCO_3$ (250 mL). The mixture was extracted with EtOAc (3×100 mL). The combined extracts were washed with brine (150 mL) then dried ($Na_2SO_4$), filtered and concentrated in vacuo to yield 2.14 g (89%) of the desired product 3.

Step 3. Alkylation of 3 to Give the Ester of 4

Sodium hydride (11 mg, 0.46 mmol) was added to a solution of alcohol 3 (100 mg, 0.40 mmol) in THF (3 mL) at 0° C. under nitrogen. After 1 h at 0° C., methyl 5-bromovalerate (67 μL, 0.47 mmol) was added and the reaction was allowed to warm to rt. After 3 h, tlc analysis showed mostly starting alcohol remaining and another portion of bromide (67 μL, 0.47 mmol) was added. After 22 h total reaction time, the reaction was quenched with 1 N HCl and extracted with EtOAc (3×25 mL). Combined extracts were dried ($Na_2SO_4$), filtered and concentrated in vacuo. Purification of the residue by flash column chromatography on silica gel (40% EtOAc/Hexane→EtOAc, gradient) afforded 19 mg (13%) of the desired ester.

Step 4. Saponification to Give 4

Aqueous lithium hydroxide (1 N, 0.5 mL) was added to a solution of ester from step 3 above (12.3 mg, 0.034 mmol) in THF (0.7 mL). After 2.5 h at rt, the reaction was acidified with 0.25 M HCl (5 mL) then extracted with $CH_2Cl_2$ (3×7 mL). Combined extracts were dried ($Na_2SO_4$), filtered and concentrated in vacuo to afford 10.2 mg (86%) of the title compound (4).

EXAMPLE 2

3-[(R)-1-(4-tert-Butyl-phenyl)-5-oxo-pyrrolidin-2-ylmethoxymethyl]-benzoic acid (5)

Step 1. Alkylation of 3 to Give the Ester of 5

Potassium hydride (23.4 mg, 0.58 mmol) and 18-crown-6 (167 mg, 0.63 mmol) were added sequentially to a solution of alcohol 3 (130 mg, 0.53 mmol) in THF (3 mL) at 0° C. After 1 h at 0° C., a solution of methyl 3-(chloromethyl)benzoate (prepared from the corresponding acid chloride, pyridine and methanol: see J. Org. Chem. 1988, 53, 2548-2552; 116 mg, 0.63 mmol) in THF (1.5 mL) was added via cannula and the reaction was allowed to warm to rt. After 22.5 h, the reaction was quenched with 0.1 N HCl (10 mL) and extracted with EtOAc (3×15 mL). Combined extracts were washed with saturated aqueous $NaHCO_3$ (15 mL) and brine (15 mL) then dried ($Na_2SO_4$), filtered and concentrated in vacuo. Purification of the residue by flash column chromatography on silica gel (30%→50% EtOAc/Hexane, gradient) afforded 66 mg (32%) of the desired ester.

Step 2. Saponification to Give 5

Aqueous lithium hydroxide (1 N, 0.4 mL) was added to a solution of ester from step 1 above (33.5 mg, 0.085 mmol) in THF (0.75 mL). After 3.5 h at rt, the reaction was acidified with 0.25 M HCl (5 mL) then extracted with $CH_2Cl_2$ (3×10 mL). Combined extracts were dried ($Na_2SO_4$), filtered and concentrated in vacuo. Purification of the residue by flash column chromatography on silica gel (2% MeOH/$CH_2Cl_2$), followed by preparative thin layer chromatography (10% MeOH/$CH_2Cl_2$) afforded 6.6 mg (20%) of the title compound (5).

EXAMPLE 3

5-[(R1)-1-(4-tert-Butyl-phenyl)-5-oxo-pyrrolidin-2-ylmethoxymethyl]-furan-2-carboxylic acid (6)

Step 1. Alkylation of 3 to Give the Ester of 6

Potassium hydride (27 mg, 0.67 mmol) and 18-crown-6 (193 mg, 0.73 mmol) were added sequentially to a solution of alcohol 3 (150 mg, 0.61 mmol) in THF (4 mL) at 0° C. After 1 h at 0° C., a solution of ethyl 5-chloromethylfuran-2-carboxylate (commercially available from Aldrich Chemical Company, 138 mg, 0.73 mmol) in THF (1 mL) was added via cannula and the reaction was allowed to warm to rt. After 18.5 h, the reaction was quenched with 0.25 N HCl (10 mL) and extracted with EtOAc (3×15 mL). Combined extracts were washed with brine (20 mL) then dried ($Na_2SO_4$), filtered and concentrated in vacuo. Purification of the residue by flash column chromatography on silica gel (20%→50% EtOAc/Hexane, gradient) afforded 78 mg (32%) of the desired ester.

Step 2. Saponification to Give 6

Aqueous lithium hydroxide (1 N, 0.5 mL) was added to a solution of ester from step 1 above (66.7 mg, 0.17 mmol) in THF (0.5 mL). After 3 h at rt, the reaction was acidified with 1 N HCl (2 mL) then extracted with $CH_2Cl_2$ (3×10 mL).

Combined extracts were dried (Na$_2$SO$_4$), filtered and concentrated in vacuo to afford 54.4 mg (88%) of the title compound (6).

EXAMPLE 4

5-[(R)-1-(4-tert-Butyl-phenyl)-5-oxo-pyrrolidin-2-ylmethoxymethyl]-thiophene-2-carboxylic acid (7)

Step 1. Alkylation of 3 to Give the Ester of 7

Potassium hydride (25.2 mg, 0.63 mmol) and 18-crown-6 (181 mg, 0.68 mmol) were added sequentially to a solution of alcohol 3 (140 mg, 0.57 mmol) in THF (4 mL) at 0° C. After 1.5 h at 0° C., a solution of methyl 5-chloromethylthiophene-2-carboxylate (prepared according to the procedures described in WO2004/037808; 130 mg, 0.68 mmol) in THF (1.5 mL) was added via cannula and the reaction was allowed to warm to rt. After 20 h, the reaction was quenched with 0.25 N HCl (15 mL) and extracted with EtOAc (3×20 mL). Combined extracts were washed with brine (30 mL) then dried (Na$_2$SO$_4$), filtered and concentrated in vacuo. Purification of the residue by flash column chromatography on silica gel (20%→50% EtOAc/Hexane, gradient) afforded 40.7 mg (18%) of the desired ester.

Step 2. Saponification to Give 7

Aqueous lithium hydroxide (1 N, 0.4 mL) was added to a solution of ester from step 1 above (37 mg, 0.092 mmol) in THF (0.75 mL). After 18 h at rt, the reaction was acidified with 1 N HCl (7 mL) then extracted with CH$_2$Cl$_2$ (3×10 mL). Combined extracts were dried (Na$_2$SO$_4$), filtered and concentrated in vacuo to afford 22.3 mg (62%) of the title compound (7).

EXAMPLE 5

7-[(S)-1-(4-tert-Butyl-phenyl)-5-oxo-pyrrolidin-2-yl]-heptanoic acid (10)

Step 1. Oxidation of 3 to Give Aldehyde 8

Molecular sieves (4 Å, 300 mg), 4-methylmorpholine N-oxide (427 mg, 3.64 mmol) and tetrapropylammonium perruthenate (250 mg, 0.71 mmol) were added sequentially to a solution of alcohol 3 (600 mg, 2.43 mmol) in CH$_2$Cl$_2$ (15 mL) at rt. After 23 h, the reaction mixture was filtered through celite, washing with CH$_2$Cl$_2$ (10 mL). The filtrate was concentrated in vacuo. Purification of the residue by flash column chromatography on silica gel (CH$_2$Cl$_2$→10% EtOAc/CH$_2$Cl$_2$, gradient) afforded 92 mg (15%) of the desired aldehyde 8.

Step 2. Wittig Reaction of 8 to Give 9

Potassium bis(trimethylsilyl)amide (0.5 M in PhMe, 1.92 mL, 0.96 mmol) was added to a solution of aldehyde 8 (86 mg, 0.35 mmol) in THF (2 mL) at rt. After 15 min at rt, the reaction mixture was cooled to −55° C. for 10 min before a solution of 5-carboxypentyltriphenylphosphonium bromide (207 mg, 0.45 mmol) was added via cannula. After 10 min at −55° C., the reaction was allowed to warm to rt. After 18 h at rt, the reaction was quenched with saturated aqueous NH$_4$Cl (15 mL) and extracted with EtOAc (3×15 mL). Combined extracts were washed with brine (20 mL), dried (Na$_2$SO$_4$), filtered and concentrated in vacuo. Purification of the residue by preparative thin layer chromatography (5% MeOH/CH$_2$Cl$_2$) afforded 10.5 mg (9%) of desired alkene 9.

Step 3. Hydrogenation of 9 to Give 10

Palladium on carbon (10 wt. %, 2 mg) was added to a solution of alkene 9 (5.8 mg, 0.017 mmol) in MeOH (1 mL). A hydrogen atmosphere was established by evacuating and refilling with hydrogen (3×) and the reaction mixture was stirred under a balloon of hydrogen for 18 h. The reaction mixture was filtered through celite, washing with MeOH, and the filtrate was concentrated in vacuo to afford 4.1 mg (70%) of the title compound (10).

EXAMPLE 6

5-{(R)-1-[4-(1-Hydroxy-hexyl)-phenyl]-5-oxo-pyrrolidin-2-ylmethoxymethyl}-furan-2-carboxylic acid (17)

Step 1. Arylation of 1 to Give 12

A solution of amide 1 (2.89 g, 12.60 mmol) in 1,4-dioxane (20 mL) followed by a solution of 1-(4-methoxybenzyloxymethyl)-4-bromobenzene (11: for synthesis, see Allergan docket #17693; 3.88 g, 12.63 mmol) were added sequentially to a mixture of xantphos (877 mg, 1.52 mmol), Pd$_2$(dba)$_3$ (463 mg, 0.51 mmol) and Cs$_2$CO$_3$ (3.2 g, 9.82 mmol) via cannula. The reaction mixture was purged with nitrogen and then heated at reflux for 22 h. The reaction mixture was allowed to cool to rt then filtered through celite, washing with CH$_2$Cl$_2$, and the filtrate was concentrated in vacuo. Purification of the residue by flash column chromatography on silica gel (5%→25% EtOAc/Hexane, gradient) afforded 1.70 g (30%) of desired product 12.

Step 2. Deprotection of 12 to Give 13

HF-pyridine (5 mL) was added to a solution of silyl ether 12 (1.38 g, 3.03 mmol) in MeCN (15 mL) in a plastic bottle at 0° C. The reaction was stirred at 0° C. for 3 h, then was quenched with saturated aqueous NaHCO$_3$ (250 mL). The mixture was extracted with EtOAc (3×100 mL). The combined extracts were washed with brine (100 mL) then dried (Na$_2$SO$_4$), filtered and concentrated in vacuo. Purification of the residue by flash column chromatography on silica gel (1%→3% MeOH/CH$_2$Cl$_2$, gradient) afforded 464 mg (45%) of desired alcohol 13.

Step 3. Alkylation of Alcohol 13 to Give 14

Potassium hydride (44 mg, 1.10 mmol) and 18-crown-6 (365 mg, 1.38 mmol) were added sequentially to a solution of alcohol 13 (315 mg, 0.92 mmol) in THF (4 mL) at 0° C. After 1 h at 0° C., ethyl 5-chloromethylfuran-2-carboxylate (0.28 mL, 1.82 mmol) was added and the reaction was allowed to warm to rt. After 22 h, the reaction was quenched with 0.5 N HCl (20 mL) and extracted with EtOAc (3×25 mL). Combined extracts were washed with brine (50 mL) then dried (Na$_2$SO$_4$), filtered and concentrated in vacuo. Purification of the residue by flash column chromatography on silica gel (20% EtOAc/Hexane→EtOAc, gradient) afforded 148 mg (32%) of desired product 14.

Step 4. Oxidative Deprotection of 14 to Give 15 and 16

2,3-Dichloro-5,6-dicyano-1,4-benzoquinone (DDQ, 82 mg, 0.36 mmol) was added to a mixture of 14 (143 mg, 0.29 mmol) in CH$_2$Cl$_2$ (4 mL) and water (0.2 mL). After 3 h, tlc indicated that starting material remained and another portion of DDQ (82 mg, 0.36 mmol) was added. After a further 1.25 h, the reaction was quenched with saturated aqueous NaHCO$_3$ (20 mL). The mixture was extracted with EtOAc (3×20 mL). The combined extracts were washed with brine (20 mL) then dried (Na$_2$SO$_4$), filtered and concentrated in vacuo. Purification of the residue by flash column chromatography on silica gel (CH$_2$Cl$_2$→3% MeOH/CH$_2$Cl$_2$, gradient) afforded 38 mg (35%) of the desired alcohol 15 and 61 mg of impure aldehyde 16. Aldehyde 16 was further purified by preparative thin layer chromatography (5% MeOH/CH$_2$Cl$_2$) to afford 48.7 mg (45%) of aldehyde 16.

Step 5. Oxidation of 15 to Give 16

Molecular sieves (4 Å, 3 mg), 4-methylmorpholine N-oxide (12.6 mg, 0.11 mmol) and tetrapropylammonium perruthenate (2.5 mg, 0.007 mmol) were added sequentially to a solution of alcohol 15 (26.8 mg, 0.072 mmol) in CH$_2$Cl$_2$ (1.5 mL) at rt. After 20 min, the reaction mixture was filtered through celite, washing with CH$_2$Cl$_2$ (5 mL). The filtrate was concentrated in vacuo. Purification of the residue by preparative thin layer chromatography (5% MeOH/CH$_2$Cl$_2$) afforded 9.6 mg (36%) of the desired aldehyde 16.

Step 6. Grignard Reaction with 16 to Give the Ester of 17

Pentyl magnesium bromide (2.0 M in Et$_2$O, 32 μL, 0.064 mmol) was added to a solution of aldehyde 16 (21.7 mg, 0.058 mmol) in THF (0.4 mL) at −40° C. under nitrogen. After 25 min, the reaction was quenched with saturated aqueous NH$_4$Cl and extracted with CH$_2$Cl$_2$ (3×7 mL). Combined extracts were dried (Na$_2$SO$_4$), filtered and concentrated in vacuo. Purification of the residue by preparative thin layer chromatography (5% MeOH/CH$_2$Cl$_2$) afforded 10.6 mg (41%) of the desired ester.

Step 7. Saponification to Give 17

Aqueous lithium hydroxide (1 N, 0.1 mL) was added to a solution of ester from step 6 above (8.8 mg, 0.02 mmol) in THF (0.2 mL). After 1 h at rt, the reaction was acidified with 0.5 N HCl (1 mL) then extracted with CH$_2$Cl$_2$ (3×7 mL). Combined extracts were dried (Na$_2$SO$_4$), filtered and concentrated in vacuo to afford 8.2 mg (99%) of the title compound (17).

EXAMPLE 7

5-{(R)-1-[4-(1-Hydroxy-2-methyl-propyl)-phenyl]-5-oxo-pyrrolidin-2-ylmethoxymethyl}-furan-2-carboxylic acid (18)

Step 1. Grignard Reaction with 16 to Give the Ester of 18

Isopropyl magnesium chloride (2.0 M in THF, 31 μL, 0.062 mmol) was added to a solution of aldehyde 16 (20.5 mg, 0.055 mmol) in THF (0.4 mL) at −40° C. under nitrogen. After 35 min, the reaction was quenched with saturated aqueous NH$_4$Cl and extracted with CH$_2$Cl$_2$ (3×7 mL). Combined extracts were dried (Na$_2$SO$_4$), filtered and concentrated in vacuo. Purification of the residue by preparative thin layer chromatography (5% MeOH/CH$_2$Cl$_2$) afforded 5 mg (22%) of the desired ester.

Step 2. Saponification to Give 18

Aqueous lithium hydroxide (1 N, 0.05 mL) was added to a solution of the ester from step 1 above (3.1 mg, 0.007 mmol) in THF (0.15 mL). After 1 h at rt, the reaction was acidified with 0.2 N HCl (1 mL) then extracted with CH$_2$Cl$_2$ (3×7 mL). Combined extracts were dried (Na$_2$SO$_4$), filtered and concentrated in vacuo to afford 2.5 mg (86%) of the title compound (18).

EXAMPLE 8

5-{(R)-1-[4-(1-Hydroxy-2-phenyl-ethyl)-phenyl]-5-oxo-pyrrolidin-2-ylmethoxymethyl}-furan-2-carboxylic acid (19)

Step 1. Grignard Reaction with 16 to Give the Ester of 19

Benzyl magnesium chloride (2.0 M in THF, 14 μL, 0.028 mmol) was added to a solution of aldehyde 16 (9.6 mg, 0.026 mmol) in THF (0.3 mL) at −40° C. under nitrogen. After 45 min, the reaction was warmed to 0° C. After 25 min at 0° C., the reaction was quenched with saturated aqueous NH$_4$Cl and extracted with CH$_2$Cl$_2$ (3×7 mL). Combined extracts were dried (Na$_2$SO$_4$), filtered and concentrated in vacuo. Purification of the residue by preparative thin layer chromatography (7% MeOH/CH$_2$Cl$_2$) afforded 3.3 mg (28%) of the desired ester.

Step 2. Saponification to Give 19

Aqueous lithium hydroxide (1 N, 0.05 mL) was added to a solution of the ester from step 1 above (2.4 mg, 0.005 mmol) in THF (0.15 mL). After 2.5 h at rt, the reaction was acidified with 0.2 N HCl (1 mL) then extracted with CH$_2$Cl$_2$ (3×7 mL). Combined extracts were dried (Na$_2$SO$_4$), filtered and concentrated in vacuo to afford 2.2 mg (98%) of the title compound (19)

EXAMPLE 9

5-{(R)-1-[4-(1-Hydroxy-hexyl)-phenyl]-5-oxo-pyrrolidin-2-ylmethoxymethyl}-thiophene-2-carboxylic acid (23)

Step 1. Alkylation of 13 to Give 20

Potassium hydride (55.5 mg, 1.38 mmol) and 18-crown-6 (456 mg, 1.73 mmol) were added sequentially to a solution of alcohol 13 (394 mg, 1.15 mmol) in THF (5 mL) at 0° C. After 1 h at 0° C., a solution of methyl 5-chloromethylthiophene-2-carboxylate (439 mg, 2.30 mmol) in THF (2 mL) was added via cannula and the reaction was allowed to warm to rt. After 19 h, tlc analysis showed starting material remained. Another portion of KH (20 mg, 0.50 mmol) was added and the reaction was heated at 50° C. After 2 h at 50° C., the reaction was cooled and quenched with 0.5 N HCl (20 mL) and extracted with EtOAc (3×25 mL). Combined extracts were washed with brine (50 mL) then dried (Na$_2$SO$_4$), filtered and concentrated in vacuo. Purification of the residue by flash column chromatography on silica gel (15% EtOAc/Hexane→EtOAc, gradient) afforded 108 mg (19%) of desired product 20.

Step 2. Oxidative Deprotection of 20 to Give 21 and 22

DDQ (91 mg, 0.40 mmol) was added to a mixture of 20 (98 mg, 0.20 mmol) in CH$_2$Cl$_2$ (3 mL) and water (0.15 mL). After 4.5 h, the reaction was quenched with saturated aqueous NaHCO$_3$ (15 mL) and extracted with EtOAc (3×25 mL). Combined extracts were washed with brine (40 mL) then dried (Na$_2$SO$_4$), filtered and concentrated in vacuo. Purification of the residue by preparative thin layer chromatography (5% MeOH/CH$_2$Cl$_2$) afforded 14.4 mg (19%) of alcohol 21 and 16.2 mg (22%) of aldehyde 22.

Step 3. Grignard Reaction with 22 to Give the Ester of 23

Pentyl magnesium bromide (2.0 M in Et$_2$O, 22 μL, 0.044 mmol) was added to a solution of aldehyde 22 (11 mg, 0.029 mmol) in THF (0.2 mL) at −40° C. under nitrogen. After 1.5 h, the reaction was quenched with saturated aqueous NH$_4$Cl and extracted with CH$_2$Cl$_2$ (3×7 mL). Combined extracts were dried (Na$_2$SO$_4$), filtered and concentrated in vacuo. Purification of the residue by preparative thin layer chromatography (5% MeOH/CH$_2$Cl$_2$) afforded 4.8 mg (37%) of the desired ester.

Step 4. Saponification to Give 23

Rabbit liver esterase (134 units/mg, 1 mg) was added to a solution of the ester from step 3 above (3.6 mg, 0.008 mmol) in MeCN (0.1 mL) and pH 7.2 buffer (2.5 mL). After 16.5 h at rt, the reaction was diluted with MeCN (7 mL) and concentrated in vacuo. The residue was suspended in CH$_2$Cl$_2$ and filtered through a cotton plug. The filtrate was concentrated in vacuo to afford 2.0 mg (57%) of the title compound (23).

EXAMPLE 10

5-{(R)-1-[4-(1-Hydroxy-hexyl)-phenyl]-5-oxo-pyrrolidin-2-ylmethoxymethyl}-thiophene-2-carboxylic acid isopropyl ester (28)

Step 1. Arylation of 1 to Give 24

A solution of amide 1 (3.37 g, 14.7 mmol) in 1,4-dioxane (30 mL) was added to a mixture of Pd$_2$(dba)$_3$ (540 mg, 0.59 mmol), xantphos (1.02 g, 1.76 mmol) and Cs$_2$CO$_3$ (5.74 g, 17.6 mmol). A solution of 1-(1-(4-methoxybenzyloxyhexyl)-4-bromobenzene (preparation 1, 4.99 g, 13.22 mmol) in 1,4-dioxane (30 mL) was added via cannula, followed by an additional 40 mL of 1,4-dioxane. The reaction mixture was purged with nitrogen then heated at reflux overnight. After 20 h, the reaction was cooled to rt and filtered through celite, washing with CH$_2$Cl$_2$. The filtrate was concentrated in vacuo and the residue was purified by flash column chromatography on silica gel (5%→30% EtOAc/Hexane, gradient) to afford 5.79 g (83%) of the desired product 24.

Step 2. Deprotection of 24 to Give 25

HF-pyridine (7 mL) was added to a solution of silyl ether 24 (4.05 g, 7.72 mmol) in MeCN (40 mL) in a plastic bottle at 0° C. The reaction was stirred at 0° C. for 1 h, then was quenched with saturated aqueous NaHCO$_3$ (300 mL). The mixture was extracted with EtOAc (3×150 mL). The combined extracts were washed with brine (200 mL) then dried (Na$_2$SO$_4$), filtered and concentrated in vacuo. Purification of the residue by flash column chromatography on silica (CH$_2$Cl$_2$→3% MeOH/CH$_2$Cl$_2$, gradient) afforded 2.3 g (72%) of the desired alcohol 25.

Step 3. Alkylation of 25 to Give 26

Potassium hydride (155 mg, 3.86 mmol) was added to a solution of alcohol 25 (1.22 g, 2.97 mmol) in THF (7 mL) at 0° C. After 15 min at 0° C., 18-crown-6 (1.02 g, 3.86 mmol) was added. After 45 min longer at 0° C., a solution of isopropyl 5-chloromethylthiophene-2-carboxylate (preparation 2, 650 mg, 2.97 mmol) in THF (5 mL) was added via cannula. Potassium iodide (50 mg, 0.30 mmol) was added and the reaction was allowed to warm to rt. After 20 h, the reaction was quenched with 0.5 N HCl (70 mL) and extracted with EtOAc (3×100 mL). Combined extracts were washed with brine (100 mL) then dried (Na$_2$SO$_4$), filtered and concentrated in vacuo. Purification of the residue by flash column chromatography on silica gel (20% EtOAc/Hexane→EtOAc, gradient) afforded 296 mg (17%) of desired product 26 along with 747 mg (61%) of recovered starting alcohol 25.

Step 4. Oxidative Deprotection of 26 to Give 27 and 28

DDQ (93 mg, 0.41 mmol) was added to a solution of 26 (220 mg, 0.37 mmol) in CH$_2$Cl$_2$ (4 mL) and water (0.2 mL) at 0° C. under nitrogen. After 35 min, the reaction was quenched with saturated aqueous NaHCO$_3$ (30 mL) and extracted with EtOAc (3×30 mL). Combined extracts were washed with brine (50 mL) then dried (Na$_2$SO$_4$), filtered and concentrated in vacuo. Purification of the residue by flash column chromatography on silica gel (20%→70% EtOAc/Hexane, gradient) afforded 13 mg (7%) of ketone 27 and 108 mg (62%) of the title compound (28).

EXAMPLE 11

3-{(R)-1-[4-(1-Hydroxy-hexyl)-phenyl]-5-oxo-pyrrolidin-2-ylmethoxymethyl}-benzoic acid (31)

Step 1. Alkylation of 13 to Give 29

Potassium hydride (16 mg, 0.39 mmol) was added to a solution of alcohol 13 (112 mg, 0.33 mmol) in THF (1.0 mL) at 0° C. After 1 h at 0° C., 18-crown-6 (114 mg, 0.43 mmol), potassium iodide (5 mg, 0.03 mmol) and a solution of methyl 3-chloromethylbenzoate (121 mg, 0.66 mmol) in THF (0.5 mL) were added sequentially. The reaction was allowed to warm to rt. After 19 h, the reaction was quenched with 0.1 N HCl (10 mL) and extracted with EtOAc (3×10 mL). Combined extracts were washed with brine (15 mL) then dried (Na$_2$SO$_4$), filtered and concentrated in vacuo. Purification of the residue by flash column chromatography on silica gel (20% EtOAc/Hexane→EtOAc, gradient) afforded 23 mg (14%) of desired product 29.

Step 2. Oxidative Deprotection of 29 to Give 30

DDQ (23 mg, 0.10 mmol) was added to a mixture of 29 (23 mg, 0.047 mmol) in CH$_2$Cl$_2$ and water (20:1, 0.25 mL). After 3.75 h, the reaction was quenched with saturated aqueous NaHCO$_3$ (10 mL) and extracted with EtOAc (3×7 mL). Combined extracts were washed with brine (10 mL) then dried (Na$_2$SO$_4$), filtered and concentrated in vacuo. Purification of the residue by preparative thin layer chromatography (80% EtOAc/Hex) afforded 13 mg (58%) of aldehyde 30.

Step 3. Grignard Reaction with 30 to Give the Ester of 31

Pentyl magnesium bromide (2.0 M in Et$_2$O, 50 µL, 0.10 mmol) was added to a solution of aldehyde 30 (12.4 mg, 0.034 mmol) in THF (0.1 mL) at −40° C. under nitrogen. After 1 h, the reaction was quenched with saturated aqueous NH$_4$Cl (7 mL) and extracted with CH$_2$Cl$_2$ (3×7 mL). Combined extracts were dried (Na$_2$SO$_4$), filtered and concentrated in vacuo. Purification of the residue by preparative thin layer chromatography (5% MeOH/CH$_2$Cl$_2$) afforded 8.6 mg (58%) of the desired ester.

Step 4. Saponification to Give 31

Rabbit liver esterase (134 units/mg, 1 mg) was added to a solution of the ester from step 3 above (7.4 mg, 0.017 mmol) in MeCN (0.1 mL) and pH 7.2 buffer (2.5 mL). After 18 h at rt, the reaction was diluted with MeCN (7 mL) and concentrated in vacuo. Purification of the residue by preparative thin layer chromatography (5% MeOH/CH$_2$Cl$_2$) afforded 1.5 mg (21%) of the title compound (31).

EXAMPLE 12

5-{(R)-1-[4-(1-Hydroxy-pentyl)-phenyl]-5-oxo-pyrrolidin-2-ylmethoxymethyl}-thiophene-2-carboxylic acid (32)

Step 1. Grignard Reaction with 22 to Give the Ester of 32 n-Butyl magnesium chloride (2.0 M in THF, 41 µL, 0.082 mmol) was added to a solution of aldehyde 22 (20.2 mg, 0.054 mmol) in THF (0.1 mL) at −40° C. under nitrogen. After 1 h, the reaction was quenched with saturated aqueous NH$_4$Cl (10 mL) and extracted with CH$_2$Cl$_2$ (3×7 mL). Combined extracts were dried (Na$_2$SO$_4$), filtered and concentrated in vacuo. Purification of the residue by preparative thin layer chromatography (5% MeOH/CH$_2$Cl$_2$) afforded 12.3 mg (53%) of the desired ester.

Step 2. Saponification to Give 32

Rabbit liver esterase (134 units/mg, 1 mg) was added to a solution of the ester from step 1 above (11.2 mg, 0.026 mmol) in MeCN (0.1 mL) and pH 7.2 buffer (3.0 mL). After 19 h at rt, the reaction was diluted with MeCN (10 mL) and concentrated in vacuo. The residue was suspended in 5% MeOH/CH$_2$Cl$_2$ and filtered through a cotton plug. The filtrate was concentrated in vacuo to afford 10.7 mg (99%) of the title compound (32).

EXAMPLE 13

5-{(R)-1-[4-(1-Hydroxy-heptyl)-phenyl]-5-oxo-pyrrolidin-2-ylmethoxymethyl}-thiophene-2-carboxylic acid (33)

Step 1. Grignard reaction with 22 to give the ester of 33 n-Hexyl magnesium bromide (2.0 M in Et$_2$O, 100 μL, 0.20 mmol) was added to a solution of aldehyde 22 (24.6 mg, 0.054 mmol) in THF (0.12 mL) at −40° C. under nitrogen. After 1.5 h, the reaction was quenched with saturated aqueous NH$_4$Cl (10 mL) and extracted with CH$_2$Cl$_2$ (3×7 mL). Combined extracts were dried (Na$_2$SO$_4$), filtered and concentrated in vacuo. Purification of the residue by preparative thin layer chromatography (5% MeOH/CH$_2$Cl$_2$) afforded 16.3 mg (54%) of the desired ester.

Step 2. Saponification to Give 33

Rabbit liver esterase (134 units/mg, 1 mg) was added to a solution of the ester from step 1 above (13 mg, 0.028 mmol) in MeCN (0.1 mL) and pH 7.2 buffer (3.0 mL). After 18 h at rt, the reaction was diluted with MeCN (10 mL) and concentrated in vacuo. The residue was suspended in 5% MeOH/CH$_2$Cl$_2$ and filtered through a cotton plug. The filtrate was concentrated in vacuo to afford 11 mg (87%) of the title compound (33).

EXAMPLE 14

5-{(R)-1-[4-(1-Hydroxy-butyl)-phenyl]-5-oxo-pyrrolidin-2-ylmethoxymethyl}-thiophene-2-carboxylic acid (34)

Step 1. Grignard Reaction with 22 to Give the Ester of 34 n-Propyl magnesium chloride (2.0 M in Et$_2$O, 92 μL, 0.18 mmol) was added to a solution of aldehyde 22 (22.9 mg, 0.061 mmol) in THF (0.12 mL) at −40° C. under nitrogen. After 1.75 h, the reaction was quenched with saturated aqueous NH$_4$Cl (10 mL) and extracted with CH$_2$Cl$_2$ (3×7 mL). Combined extracts were dried (Na$_2$SO$_4$), filtered and concentrated in vacuo. Purification of the residue by preparative thin layer chromatography (5% MeOH/CH$_2$Cl$_2$) afforded 13 mg (51%) of the desired ester.

Step 2. Saponification to Give 34

Rabbit liver esterase (134 units/mg, 1 mg) was added to a solution of the ester from step 1 above (10.8 mg, 0.026 mmol) in MeCN (0.1 mL) and pH 7.2 buffer (3.0 mL). After 17 h at rt, the reaction was diluted with MeCN (10 mL) and concentrated in vacuo. The residue was suspended in 5% MeOH/CH$_2$Cl$_2$ and filtered through a cotton plug. The filtrate was concentrated in vacuo to afford 10.4 mg (99%) of the title compound (34).

EXAMPLE 15

5-{(R)-1-[4-(1-Hydroxy-propyl)-phenyl]-5-oxo-pyrrolidin-2-ylmethoxymethyl}-thiophene-2-carboxylic acid (35)

Step 1. Grignard Reaction with 22 to Give the Ester of 35

Ethyl magnesium chloride (2.0 M in Et$_2$O, 24 μL, 0.048 mmol) was added to a solution of aldehyde 22 (5.8 mg, 0.016 mmol) in THF (0.1 mL) at −40° C. under nitrogen. After 1.25 h, the reaction was quenched with saturated aqueous NH$_4$Cl (5 mL) and extracted with CH$_2$Cl$_2$ (3×5 mL). Combined extracts were dried (Na$_2$SO$_4$), filtered and concentrated in vacuo. Purification of the residue by preparative thin layer chromatography (5% MeOH/CH$_2$Cl$_2$) afforded 2.5 mg (40%) of the desired ester.

Step 2. Saponification to Give 35

Rabbit liver esterase (134 units/mg, 1 mg) was added to a solution of the ester from step 1 above (2.8 mg, 0.007 mmol) in MeCN (0.1 mL) and pH 7.2 buffer (2.5 mL). After 17 h at rt, the reaction was diluted with MeCN (10 mL) and concentrated in vacuo. The residue was suspended in 5% MeOH/CH$_2$Cl$_2$ and filtered through a cotton plug. The filtrate was concentrated in vacuo to afford 2.7 mg (99%) of the title compound (35).

EXAMPLE 16

5-((E and Z)-3-{(R)-1-[4-(1-Hydroxy-hexyl)-phenyl]-5-oxo-pyrrolidin-2-yl}-allyl)-thiophene-2-carboxylic acid (41)

Step 1. Oxidation of 25 to Give Aldehyde 36

Dess-Martin periodinane (1.63 g, 3.83 mmol) was added to a solution of alcohol 25 (1.43 g, 3.48 mmol) in CH$_2$Cl$_2$ (12 mL) at rt under nitrogen. After 1 h at rt the reaction was quenched with saturated aqueous NaHCO$_3$ and saturated aqueous NaHSO$_3$ (1:1100 mL). The mixture was extracted with CH$_2$Cl$_2$ (3×150 mL). The combined extracts were dried (Na$_2$SO$_4$), filtered and concentrated in vacuo. Purification of the residue by flash column chromatography on silica (2% MeOH/CH$_2$Cl$_2$) afforded 915 mg (64%) of the desired aldehyde 36.

Step 2. Methylenation of 36 to Give Alkene 37

The Tebbe reagent (0.5 M in THF, 4.86 mL, 2.43 mmol) was added to a solution of aldehyde 36 (677 mg, 1.65 mmol) in THF (11 mL) at −40° C. under nitrogen. After 1 h at −40° C. the reaction was quenched by addition of aqueous 2 N NaOH (1.65 mL) and stirred vigorously overnight with the addition of THF (15 mL). The mixture was filtered through celite, washing with excess EtOAc. The filtrate was concentrated in vacuo. Purification of the residue by flash column chromatography on silica (30%→50% EtOAc/Hex) afforded 254 mg (38%) of the desired alkene 37.

Step 3. Metathesis Reaction of 37 to Give Alkene 38

Benzylidene[1,3-bis(2,4,6-trimethylphenyl)-2-imidazolidinylidene]dichloro(tricyclohexylphosphine)-ruthenium (Grubbs' catalyst, 2nd generation, 48 mg, 0.057 mmol) was added to a solution of alkene 37 (230 mg, 0.56 mmol) and methyl 5-allylthiophene-2-carboxylate (preparation 3, 206 mg, 1.13 mmol) in $CH_2Cl_2$ (3.0 mL). The reaction mixture was heated at reflux for 4 h. The reaction mixture was cooled to rt and more catalyst (48 mg, 0.057 mmol) and methyl 5-allylthiophene-2-carboxylate (100 mg, 0.55 mmol) were added. The mixture was heated for 18 h longer at reflux then cooled and concentrated in vacuo. Purification of the residue by flash column chromatography on silica (5%→50% EtOAc/Hex, gradient) afforded 100 mg (32%) of the desired alkene 38 along with 130 mg (57%) of the starting alkene 37.

Step 4. Oxidative Deprotection of 38 to Give 39 and 40

DDQ (58 mg, 0.26 mmol) was added to a mixture of 38 (130 mg, 0.23 mmol) in $CH_2Cl_2$ (3.1 mL) and water (0.16 mL) at 0° C. under nitrogen. After 45 min, the reaction was quenched with saturated aqueous $NaHCO_3$ (40 mL). The mixture was extracted with EtOAc (3×30 mL). The combined extracts were washed with brine (25 mL) then dried ($Na_2SO_4$), filtered and concentrated in vacuo. Purification of the residue by flash column chromatography on silica (50%→75% EtOAc/Hex, gradient) afforded 28 mg of an inseparable mixture of starting material 38 and ketone 39, and 63 mg (62%) of the desired alcohol 40.

Step 5. Saponification of 40 to Give 41

Rabbit liver esterase (134 units/mg, 1 mg) was added to a solution of ester 40 (3.7 mg, 0.008 mmol) in MeCN (0.2 mL) and pH 7.2 buffer (2.5 mL). After 15.5 h at rt, the reaction was diluted with MeCN (8 mL) and concentrated in vacuo. The residue was suspended in 10% MeOH/$CH_2Cl_2$ and filtered through a cotton plug. The filtrate was concentrated in vacuo to afford 3.0 mg (84%) of the title compound (41).

EXAMPLE 17

5-(3-{(S)-1-[4-(1-Hydroxy-hexyl)-phenyl]-5-oxo-pyrrolidin-2-yl}-propyl)-thiophene-2-carboxylic acid (43)

Step 1. Hydrogenation of 40 to Give Ester 42

Palladium on carbon (10 wt. %, 15 mg) was added to a solution of alkene 40 (63 mg, 0.14 mmol) in methanol (3.0 mL). A hydrogen atmosphere was established by evacuating and refilling with hydrogen (3×) and the reaction mixture was stirred under a balloon of hydrogen. After 3 h at rt, the reaction mixture was filtered through celite, washing with MeOH, and the filtrate was concentrated in vacuo to afford 63 mg crude product. $^1$H NMR analysis showed starting material remaining so the crude material was resubmitted to the conditions above. After 20 h at rt, the reaction mixture was filtered through celite, washing with MeOH, and the filtrate was concentrated in vacuo to afford 60 mg (95%) of the desired ester 42.

Step 2. Saponification of 42 to give 43.

Aqueous 1 N lithium hydroxide (0.19 mL, 0.19 mmol) was added to a solution of ester 42 (17 mg, 0.038 mmol) in THF (0.38 mL). After 20 h at rt, $H_2O$ (1.0 mL) was added and the mixture was acidified with 1 N aqueous HCl (1.0 mL) and extracted with EtOAc (3×10 mL). The combined extracts were washed with brine (10 mL) then dried ($Na_2SO_4$), filtered and concentrated in vacuo. Purification of the residue by flash column chromatography on silica (EtOAc→25% MeOH/EtOAc, gradient) afforded 14.4 mg (87%) of the title compound (43).

EXAMPLE 18

5-(3-{(S)-1-[4-(1-Hydroxy-hexyl)-phenyl]-5-oxo-pyrrolidin-2-yl}-propyl)-thiophene-2-carboxylic acid isopropyl ester (44)

DBU (5.2 µL, 0.035 mmol) was added to a solution of acid 43 (7.5 mg, 0.017 mmol) in acetone (0.1 mL) at rt under nitrogen. After 10 min, 2-iodopropane (35 µL, 0.35 mmol) was added. After 21 h at rt, the reaction was quenched with 0.01 N HCl (3 mL) and extracted with EtOAc (3×4 mL). The combined extracts were washed with brine (5 mL), dried ($Na_2SO_4$), filtered and concentrated in vacuo. Purification of the residue by flash column chromatography on silica ($CH_2Cl_2$→1% MeOH/$CH_2Cl_2$) afforded 4.6 mg (53%) of the title compound (44).

EXAMPLE 19

5-{3-[(S)-1-(4-Hexanoyl-phenyl)-5-oxo-pyrrolidin-2-yl]-propyl}-thiophene-2-carboxylic acid (46)

Step 1. Oxidation of 38/39 Afford 39

DDQ (5.5 mg, 0.024 mmol) was added to the mixture of ether 38 and ketone 39 from Example 16, step 4 (6.8 mg, 0.012 mmol) in $CH_2Cl_2$ and water (20:1, 0.25 mL) at rt under nitrogen. After 1.5 h, the reaction was quenched with saturated aqueous $NaHCO_3$ (5 mL). The mixture was extracted with EtOAc (3×5 mL). The combined extracts were washed with brine (5 mL) then dried ($Na_2SO_4$), filtered and concentrated in vacuo. Purification of the residue by preparative thin layer chromatography (60% EtOAc/Hex) afforded 1.5 mg (28%) of desired ketone 39.

Step 2. Hydrogenation of 39 to Give Ester 45

Palladium on carbon (10 wt. %, 1 mg) was added to a solution of alkene 39 (1.5 mg, 0.0034 mmol) in methanol (0.5 mL). A hydrogen atmosphere was established by evacuating and refilling with hydrogen (3×) and the reaction mixture was stirred under a balloon of hydrogen. After 2 h at rt, the reaction mixture was filtered through celite, washing with MeOH, and the filtrate was concentrated in vacuo to afford 1.3 mg (86%) of desired ester 45.

Step 3. Saponification of 45 to Give 46

Rabbit liver esterase (134 units/mg, 1 mg) was added to a solution of ester 45 (1.3 mg, 0.0029 mmol) in MeCN (0.1 mL) and pH 7.2 buffer (2.5 mL). After 23 h at rt, the reaction was diluted with MeCN (10 mL) and concentrated in vacuo. The residue was suspended in 10% MeOH/$CH_2Cl_2$ and filtered through a cotton plug. The filtrate was concentrated in vacuo to afford 1.2 mg (95%) of the title compound (46).

EXAMPLE 20

5-[(R)-1-(4-Hexanoyl-phenyl)-5-oxo-pyrrolidin-2-ylmethoxymethyl]-thiophene-2-carboxylic acid (47)

Rabbit liver esterase (134 units/mg, 1 mg) was added to a solution of ester 27 (Example 10, step 4, 6.6 mg, 0.014 mmol) in MeCN (0.1 mL) and pH 7.2 buffer (2.5 mL). After 17 h at rt, the reaction was diluted with MeCN (8 mL) and concentrated in vacuo. Purification of the residue by preparative thin layer chromatography (4% MeOH/CH$_2$Cl$_2$) afforded 1 mg (17%) of the title compound (47).

EXAMPLES 21 AND 22

5-{(R)-1-[4-(1-Hydroxy-hexyl)-phenyl]-5-oxo-pyrrolidin-2-ylmethoxymethyl}-thiophene-2-carboxylic acid isopropyl ester (faster eluting diastereomer 48) and 5-{(R)-1-[4-(1-Hydroxy-hexyl)-phenyl]-5-oxo-pyrrolidin-2-ylmethoxymethyl}-thiophene-2-carboxylic acid isopropyl ester (slower eluting diastereomer 49)

The two diastereomers of example 10 (28, ~100 mg) were separated on a Waters 600 HPLC instrument employing a Waters 2996 PDA detector and a Whatman Partisil® 10 M20/50 column, 22 mm×500 mm (Cat. No. 4232-220, Q.A. No. 3TA02D80). Using 60% EtOAc/Hex as the eluent and a flow rate of 15 mL/min, the first diastereomer (48, 32.8 mg total isolated) eluted at 55-60 min, and the second diastereomer (49, 52.6 mg total isolated) eluted at 61-70 min.

EXAMPLE 23

5-{(R)-1-[4-(1-Hydroxy-hexyl)-phenyl]-5-oxo-pyrrolidin-2-ylmethoxymethyl}-thiophene-2-carboxylic acid (50)

Aqueous 1 N lithium hydroxide (0.05 mL, 0.05 mmol) was added to a solution of faster eluting ester diastereomer 48 (2.7 mg, 0.0057 mmol) in THF (0.1 mL) and the mixture was heated at reflux overnight. After 17 h, the reaction was cooled to rt, acidified with 0.05 N aqueous HCl (5 mL) and extracted with CH$_2$Cl$_2$ (3×5 mL). The combined extracts were dried (Na$_2$SO$_4$), filtered and concentrated in vacuo to afford 2.5 mg (100%) of the title compound (50).

EXAMPLE 24

5-{(R)-1-[4-(1-Hydroxy-hexyl)-phenyl]-5-oxo-pyrrolidin-2-ylmethoxymethyl}-thiophene-2-carboxylic acid (51)

Aqueous 1 N lithium hydroxide (0.05 mL, 0.05 mmol) was added to a solution of slower eluting ester diastereomer 49 (2.8 mg, 0.0059 mmol) in THF (0.1 mL) and the mixture was heated at reflux overnight. After 23 h, the reaction was cooled to rt, acidified with 0.05 N aqueous HCl (5 mL) and extracted with CH$_2$Cl$_2$ (3×5 mL). The combined extracts were dried (Na$_2$SO$_4$), filtered and concentrated in vacuo to afford 1.7 mg (67%) of the title compound (51).

EXAMPLES 25 AND 26

5-(3-{(S)-1-[4-(1-Hydroxy-hexyl)-phenyl]-5-oxo-pyrrolidin-2-yl}-propyl)-thiophene-2-carboxylic acid methyl ester (faster eluting diastereomer 52) and 5-(3-{(S)-1-[4-(1-hydroxy-hexyl)-phenyl]-5-oxo-pyrrolidin-2-yl}-propyl)-thiophene-2-carboxylic acid methyl ester (slower eluting diastereomer 53)

The two diastereomers from example 17, step 1 (42, ~43 mg) were separated on a Waters 600 HPLC instrument employing a Waters 2996 PDA detector and a Whatman Partisil® 10 M20/50 column, 22 mm×500 mm (Cat. No. 4232-220, Q.A. No. 3TA02D80). Using 55% EtOAc/Hex as the eluent and a flow rate of 15 mL/min, the first diastereomer (52, 16 mg) eluted at 69-75 min, and the second diastereomer (53, 19 mg) eluted at 80-88 min.

EXAMPLE 27

5-(3-{(S)-1-[4-(1-Hydroxy-hexyl)-phenyl]-5-oxo-pyrrolidin-2-yl}-propyl)-thiophene-2-carboxylic acid (54)

Rabbit liver esterase (134 units/mg, 2 mg) was added to a solution of faster eluting ester diastereomer 52 (16 mg, 0.036 mmol) in MeCN (0.2 mL) and pH 7.2 buffer (3.0 mL). After 18 h at rt, the reaction was diluted with MeCN (10 mL) and concentrated in vacuo. The residue was diluted with CH$_2$Cl$_2$ (5 mL), filtered through a plug of glass wool and concentrated in vacuo. Purification of the residue by preparative thin layer chromatography (EtOAc→25% MeOH/EtOAc, gradient) afforded 12 mg (77%) of the title compound (54).

EXAMPLE 28

5-(3-{(S)-1-[4-(1-Hydroxy-hexyl)-phenyl]-5-oxo-pyrrolidin-2-yl}-propyl)-thiophene-2-carboxylic acid (55)

Rabbit liver esterase (134 units/mg, 2 mg) was added to a solution of slower eluting ester diastereomer 53 (19 mg, 0.043 mmol) in MeCN (0.2 mL) and pH 7.2 buffer (3.0 mL). After 18 h at rt, the reaction was diluted with MeCN (10 mL) and concentrated in vacuo. The residue was diluted with CH$_2$Cl$_2$ (5 mL), filtered through a plug of glass wool and concentrated in vacuo. Purification of the residue by preparative thin layer chromatography (EtOAc→25% MeOH/EtOAc, gradient) afforded 10.5 mg (57%) of the title compound (55).

EXAMPLE 29

5-(3-{(S)-1-[4-(1-Hydroxy-hexyl)-phenyl]-5-oxo-pyrrolidin-2-yl}-propyl)-thiophene-2-carboxylic acid isopropyl ester (56, from 54 and 52)

DBU (4.2 µL, 0.028 mmol) and 2-iodopropane (19 µL, 0.19 mmol) were added to a solution of acid 54 (8 mg, 0.019 mmol) in acetone (0.15 mL) at rt under nitrogen. After 18 h at rt, the solvent was removed under a stream of nitrogen. The residue was diluted with EtOAc (10 mL) and washed with 0.1 N HCl (2×5 mL) and brine (5 mL) then dried (Na$_2$SO$_4$), filtered and concentrated in vacuo. Purification of the residue by flash column chromatography on silica (CH$_2$Cl$_2$→5% MeOH/CH$_2$Cl$_2$) afforded 1.9 mg (22%) of the title compound (56) and 4 mg (50%) recovered 54.

EXAMPLE 30

5-(3-{(S)-1-[4-(1-Hydroxy-hexyl)-phenyl]-5-oxo-pyrrolidin-2-yl}-propyl)-thiophene-2-carboxylic acid isopropyl ester (57, from 55 and 53)

DBU (4.7 µL, 0.031 mmol) and 2-iodopropane (21 µL, 0.21 mmol) were added to a solution of acid 55 (9 mg, 0.021 mmol) in acetone (0.2 mL) at rt under nitrogen. After 18 h at rt, the solvent was removed under a stream of nitrogen. The residue was diluted with EtOAc (10 mL) and washed with 0.1 N HCl (2×5 mL) and brine (5 mL) then dried (Na$_2$SO$_4$), filtered and concentrated in vacuo. Purification of the residue by flash column chromatography on silica (CH$_2$Cl$_2$→25%

MeOH/CH$_2$Cl$_2$) afforded 2.0 mg (20%) of the title compound (57) and 6 mg (67%) recovered 55.

EXAMPLE 31

5-{(R)-1-[4-(1-Hydroxy-heptyl)-phenyl]-5-oxo-pyrrolidin-2-ylmethoxymethyl}-thiophene-2-carboxylic acid isopropyl ester (61)

Step 1. Arylation of 1 to Give 58

Pd$_2$(dba)$_3$ (550 mg, 0.60 mmol), xantphos (1.04 g, 180 mmol) and Cs$_2$CO$_3$ (5.87 g, 18.0 mmol) were added sequentially to a solution of amide 1 (3.45 g, 15.0 mmol) in 1,4-dioxane (100 mL). A solution of 1-(1-(4-methoxybenzyloxy-heptyl)-4-bromobenzene (preparation 4, 5.30 g, 13.54 mmol) in 1,4-dioxane (50 mL) was added via cannula. The reaction mixture was purged with nitrogen then heated at reflux overnight. After 17 h, the reaction was cooled to rt and filtered through celite, washing with CH$_2$Cl$_2$. The filtrate was concentrated in vacuo and the residue was purified by flash column chromatography on silica gel (5%→35% EtOAc/Hexane, gradient) to afford 5.26 g (72%) of the desired product 58.

Step 2. Deprotection of 58 to Give 59

HF-pyridine (8.8 mL) was added to a solution of silyl ether 58 (5.26 g, 9.74 mmol) in MeCN (50 mL) in a plastic bottle at 0° C. After 45 min at 0° C., the reaction was quenched with saturated aqueous NaHCO$_3$ (400 mL). The mixture was extracted with EtOAc (3×200 mL). The combined extracts were washed with brine (200 mL) then dried (Na$_2$SO$_4$), filtered and concentrated in vacuo. Purification of the residue by flash column chromatography on silica (CH$_2$Cl$_2$→5% MeOH/CH$_2$Cl$_2$, gradient) afforded 3.9 g (94%) of the desired alcohol 59 as a pale yellow solid.

Step 3. Alkylation of 59 to Give 60

A round bottom flask was charged with potassium hydride (30 wt % in oil, 138 mg, 1.03 mmol). The material was washed with hexanes (3×1 mL), then suspended in THF (1 mL). The mixture was cooled to 0° C. and a solution of alcohol 59 (339 mg, 0.80 mmol) in THF (1.5 mL) was added via cannula. After 1 h at 0° C., a solution of isopropyl 5-chloromethylthiophene-2-carboxylate (preparation 2, 174 mg, 0.80 mmol) in THF (1.5 mL) was added via cannula. Potassium iodide (14 mg, 0.08 mmol) was added and the reaction was allowed to warm to rt. After 18 h, the reaction was quenched with saturated aqueous NH$_4$Cl (15 mL) and extracted with EtOAc (3×25 mL). Combined extracts were washed with brine (15 mL) then dried (Na$_2$SO$_4$), filtered and concentrated in vacuo. Purification of the residue by flash column chromatography on silica gel (20%→75% EtOAc/Hexane, gradient), followed by preparative thin layer chromatography (65% EtOAc/Hexane) afforded 65 mg (14%) of desired product 60.

Step 4. Oxidative Deprotection of 60 to Give 61

DDQ (26 mg, 0.12 mmol) was added to a solution of 60 (65 mg, 0.11 mmol) in CH$_2$Cl$_2$ (1.4 mL) and water (0.07 mL) at 0° C. under nitrogen. After 40 min, the reaction was quenched with saturated aqueous NaHCO$_3$ (20 mL) and extracted with EtOAc (3×20 mL). Combined extracts were washed with brine (15 mL) then dried (Na$_2$SO$_4$), filtered and concentrated in vacuo. Purification of the residue by flash column chromatography on silica gel (50%→75% EtOAc/Hexane, gradient), followed by preparative thin layer chromatography (60% EtOAc/Hexane) afforded 36 mg (69%) of the title compound (61).

EXAMPLES 32 AND 33

5-{(R)-1-[4-(1-Hydroxy-heptyl)-phenyl]-5-oxo-pyrrolidin-2-ylmethoxymethyl}-thiophene-2-carboxylic acid isopropyl ester (faster eluting diastereomer 62) and 5-{(R)-1-[4-(1-hydroxy-heptyl)-phenyl]-5-oxo-pyrrolidin-2-ylmethoxymethyl}-thiophene-2-carboxylic acid isopropyl ester (slower eluting diastereomer 63)

The two diastereomers of example 31 (61, ~36 mg) were separated on a Waters 600 HPLC instrument employing a Waters 2996 PDA detector and a Whatman Partisil® 10 M20/50 column, 22 mm×500 mm (Cat. No. 4232-220, Q.A. No. 3TA02D80). Using 60% EtOAc/Hex as the eluent and a flow rate of 15 mL/min, the first diastereomer (62, 14.8 mg) eluted at 50-56.5 min, and the second diastereomer (63, 16.4 mg) eluted at 56.5-70 min.

EXAMPLE 34

5-{(R)-1-[4-(1-Hydroxy-heptyl)-phenyl]-5-oxo-pyrrolidin-2-ylmethoxymethyl}-thiophene-2-carboxylic acid (64)

Aqueous 1 N lithium hydroxide (0.05 mL, 0.05 mmol) was added to a solution of faster eluting ester diastereomer 62 (3.5 mg, 0.0072 mmol) in THF (0.1 mL) and the mixture was heated at reflux overnight. After 18 h, the reaction was cooled to rt, diluted with water (2 mL), acidified with 1.0 N aqueous HCl (1 mL) and extracted with EtOAc (3×5 mL). The combined extracts were washed with brine (5 mL), dried (Na$_2$SO$_4$), filtered and concentrated in vacuo to afford 3.0 mg (94%) of the title compound (64).

EXAMPLE 35

5-{(R)-1-[4-(1-Hydroxy-heptyl)-phenyl]-5-oxo-pyrrolidin-2-ylmethoxymethyl}-thiophene-2-carboxylic acid (65)

Aqueous 1 N lithium hydroxide (0.05 mL, 0.05 mmol) was added to a solution of slower eluting ester diastereomer 63 (3.5 mg, 0.0072 mmol) in THF (0.1 mL) and the mixture was heated at reflux overnight. After 18 h, the reaction was cooled to rt, diluted with water (2 mL), acidified with 1.0 N aqueous HCl (1 mL) and extracted with EtOAc (3×5 mL). The combined extracts were washed with brine (5 mL), dried (Na$_2$SO$_4$), filtered and concentrated in vacuo to afford 3.2 mg (99%) of the title compound (65).

EXAMPLE 36

5-(3-{(S)-1-[4-(1-Hydroxy-heptyl)-phenyl]-5-oxo-pyrrolidin-2-yl}-propyl)-thiophene-2-carboxylic acid (71)

Step 1. Oxidation of 59 to Give Aldehyde 66

1-(3-(Dimethylaminopropyl)-3-ethylcarbodiimide hydrochloride (EDCI, 1.43 g, 7.45 mmol) and DMSO (0.70 mL, 9.86 mmol) were added sequentially to a solution of alcohol 59 (1.06 g, 2.48 mmol) in benzene (25 mL) at rt under nitrogen. After 10 min at rt, pyridinium trifluoroacetate (527 mg, 2.73 mmol) was added. After 3 h at rt, the solution was decanted from the oily residue and the residue was washed with benzene (3×15 mL). The combined benzene phases were concentrated in vacuo. Purification of the residue by flash column chromatography on silica (CH$_2$Cl$_2$→3% MeOH/CH$_2$Cl$_2$, gradient) afforded 1.0 g (95%) of the desired aldehyde 66.

Step 2. Methylenation of 66 to Give Alkene 67

The Tebbe reagent (0.5 M in THF, 7.0 mL, 3.5 mmol) was added to a solution of aldehyde 66 (1.0 g, 2.36 mmol) in THF (16 mL) at −40° C. under nitrogen. After 1 h at −40° C. the reaction was quenched by addition of aqueous 2 N NaOH (5.25 mL) and stirred vigorously overnight with the addition of THF (20 mL). The mixture was filtered through celite, washing with excess EtOAc. The filtrate was concentrated in vacuo. Purification of the residue by flash column chromatography on silica (40% EtOAc/Hex) afforded 195 mg (20%) of the desired alkene 67.

Step 3. Metathesis Reaction of 67 to Give Alkene 68

Grubbs' second generation catalyst (38 mg, 0.045 mmol) was added to a solution of alkene 67 (190 mg, 0.45 mmol) and methyl 5-allylthiophene-2-carboxylate (preparation 3, 173 mg, 0.95 mmol) in CH$_2$Cl$_2$ (2.4 mL). The reaction mixture was heated at reflux for 2 h. The reaction mixture was cooled to rt and more catalyst (9 mg, 0.011 mmol) and methyl 5-allylthiophene-2-carboxylate (165 mg, 0.91 mmol) were added. The mixture was heated for 22 h longer at reflux then cooled and concentrated in vacuo. Purification of the residue by flash column chromatography on silica (2 times, first using 5%→50% EtOAc/Hex, gradient then second using CH$_2$Cl$_2$→3% MeOH/CH$_2$Cl$_2$, gradient) afforded 180 mg (69%) of the desired alkene 68.

Step 4. Oxidative Deprotection of 68 to Give 69

DDQ (78 mg, 0.34 mmol) was added to a mixture of 68 (180 mg, 0.31 mmol) in CH$_2$Cl$_2$ (4.1 mL) and water (0.21 mL) at 0° C. under nitrogen. After 45 min at 0° C., the reaction was quenched with saturated aqueous NaHCO$_3$ (50 mL). The mixture was extracted with EtOAc (3×50 mL). The combined extracts were washed with brine (50 mL) then dried (Na$_2$SO$_4$), filtered and concentrated in vacuo. Purification of the residue by flash column chromatography on silica (50%→66% EtOAc/Hex, gradient) afforded 50 mg (35%) of the desired alcohol 69.

Step 5. Hydrogenation of 69 to Give Ester 70

Palladium on carbon (10 wt. %, 12 mg) was added to a solution of alkene 69 (50 mg, 0.11 mmol) in methanol (2.3 mL). A hydrogen atmosphere was established by evacuating and refilling with hydrogen (3×) and the reaction mixture was stirred under a balloon of hydrogen. After 20 h at rt, the reaction mixture was filtered through celite, washing with MeOH, and the filtrate was concentrated in vacuo to afford 50 mg (99%) of the desired ester 70.

Step 6. Saponification of 70 to Give 71

Aqueous 1 N lithium hydroxide (0.19 mL, 0.19 mmol) was added to a solution of ester 70 (17 mg, 0.038 mmol) in THF (0.4 mL). After 18 h at rt, H$_2$O (1.0 mL) was added and the mixture was acidified with 1 N aqueous HCl (1.0 mL) and extracted with EtOAc (3×10 mL). The combined extracts were washed with brine (10 mL) then dried (Na$_2$SO$_4$), filtered and concentrated in vacuo. Purification of the residue by preparative thin layer chromatography (15% MeOH/CH$_2$Cl$_2$) afforded 5.6 mg (34%) of the title compound (71).

EXAMPLES 37 AND 38

5-(3-{(S)-1-[4-(1-Hydroxy-heptyl)-phenyl]-5-oxo-pyrrolidin-2-yl}-propyl)-thiophene-2-carboxylic acid methyl ester (faster eluting diastereomer 72) and
5-(3-{(S)-1-[4-(1-hydroxy-heptyl)-phenyl]-5-oxo-pyrrolidin-2-yl}-propyl)-thiophene-2-carboxylic acid methyl ester (slower eluting diastereomer 73)

The two diastereomers from example 36, step 5 (70, ~34 mg) were separated on a Waters 600 HPLC instrument employing a Waters 2996 PDA detector and a Whatman Partisil® 10 M20/50 column, 22 mm×500 mm (Cat. No. 4232-220, Q.A. No. 3TA02D80). Using 55% EtOAc/Hex as the eluent and a flow rate of 15 mL/min, the first diastereomer (72, 10.7 mg) eluted at 78-87.5 min, and the second diastereomer (73, 7.0 mg) eluted at 91-101 min.

EXAMPLE 39

5-(3-{(S)-1-[4-(1-Hydroxy-heptyl)-phenyl]-5-oxo-pyrrolidin-2-yl}-propyl)-thiophene-2-carboxylic acid (74)

Aqueous 1 N lithium hydroxide (0.12 mL, 0.12 mmol) was added to a solution of faster eluting ester diastereomer 72 (10.7 mg, 0.023 mmol) in THF (0.3 mL). After 66 h at rt, H$_2$O (1.0 mL) was added and the mixture was acidified with 1 N aqueous HCl (1.0 mL) and extracted with EtOAc (3×10 mL). The combined extracts were washed with brine (5 mL) then dried (Na$_2$SO$_4$), filtered and concentrated in vacuo to afford 10 mg (96%) of the title compound (74).

EXAMPLE 40

5-(3-{(S)-1-[4-(1-Hydroxy-heptyl)-phenyl]-5-oxo-pyrrolidin-2-yl}-propyl)-thiophene-2-carboxylic acid (75)

Aqueous 1 N lithium hydroxide (0.08 mL, 0.08 mmol) was added to a solution of slower eluting ester diastereomer 73 (7.0 mg, 0.015 mmol) in THF (0.2 mL). After 66 h at rt, H$_2$O (1.0 mL) was added and the mixture was acidified with 1 N aqueous HCl (1.0 mL) and extracted with EtOAc (3×8 mL). The combined extracts were washed with brine (5 mL) then dried (Na$_2$SO$_4$), filtered and concentrated in vacuo to afford 6.5 mg (96%) of the title compound (75).

EXAMPLE 41

5-(3-{(S)-1-[4-(1-Hydroxy-heptyl)-phenyl]-5-oxo-pyrrolidin-2-yl}-propyl)-thiophene-2-carboxylic acid isopropyl ester (76, from 74 and 72)

DBU (4.0 μL, 0.027 mmol) and 2-iodopropane (36 μL, 0.36 mmol) were added to a solution of acid 74 (8 mg, 0.018 mmol) in acetone (0.2 mL) at rt under nitrogen. After 72 h at rt, the solvent was removed under a stream of nitrogen. The residue was diluted with EtOAc (10 mL) and washed with 0.5 N HCl (2×5 mL) and brine (5 mL) then dried (Na$_2$SO$_4$), filtered and concentrated in vacuo. Purification of the residue by flash column chromatography on silica (EtOAc→20% MeOH/EtOAc) afforded 7.3 mg (83%) of the title compound (76).

EXAMPLE 42

5-(3-{(S)-1-[4-(1-Hydroxy-heptyl)-phenyl]-5-oxo-pyrrolidin-2-yl}-propyl)-thiophene-2-carboxylic acid isopropyl ester (77, from 75 and 73)

DBU (2.5 µL, 0.017 mmol) and 2-iodopropane (22.5 µL, 0.225 mmol) were added to a solution of acid 75 (5 mg, 0.011 mmol) in acetone (0.11 mL) at rt under nitrogen. After 72 h at rt, the solvent was removed under a stream of nitrogen. The residue was diluted with EtOAc (10 mL) and washed with 0.5 N HCl (2×5 mL) and brine (5 mL) then dried ($Na_2SO_4$), filtered and concentrated in vacuo. Purification of the residue by flash column chromatography on silica (EtOAc→20% MeOH/EtOAc) afforded 3.2 mg (58%) of the title compound (77).

EXAMPLE 43

4-{(R)-1-[4-(1-Hydroxy-hexyl)-phenyl]-5-oxo-pyrrolidin-2-ylmethoxy}-benzoic acid (80)

Step 1. Mitsunobu Reaction of 25 and Methyl 4-Hydroxybenzoate to Give 78

Diisopropyl azodicarboxylate (DIAD, 194 µL, 1.0 mmol) was added to a solution of alcohol 25 (200 mg, 0.49 mmol), triphenylphosphine (191 mg, 0.73 mmol) and methyl 4-hydroxybenzoate (87 mg, 0.57 mmol) in $CH_2Cl_2$ (2.5 mL). After stirring 18 h at rt, the solvent was removed under a stream of nitrogen and the residue was suspended in EtOAc (75 mL). The mixture was washed with saturated aqueous $NaHCO_3$ (3×25 mL) and brine (25 mL) then the organic phase was dried ($Na_2SO_4$) filtered and concentrated in vacuo. Purification of the residue by flash column chromatography on silica gel (50% EtOAc/hexane →EtOAc, gradient) afforded 81 mg (31%) of the desired ether 78.

Step 2. Oxidative Deprotection of 78 to Give 79

DDQ (37 mg, 0.16 mmol) was added to a mixture of 78 (81 mg, 0.15 mmol) in $CH_2Cl_2$ (2.0 mL) and water (0.1 mL) at 0° C. under nitrogen. After 45 min at 0° C., the reaction was quenched with saturated aqueous $NaHCO_3$ (25 mL). The mixture was extracted with EtOAc (3×25 mL). The combined extracts were washed with brine (25 mL) then dried ($Na_2SO_4$), filtered and concentrated in vacuo. Purification of the residue by flash column chromatography on silica (85% EtOAc/Hex→EtOAc, gradient) afforded 31 mg (49%) of the desired alcohol 79.

Step 3. Saponification of 79 to Give 80

Aqueous 1 N lithium hydroxide (0.35 mL, 0.35 mmol) was added to a solution of ester 79 (30 mg, 0.071 mmol) in THF (0.7 mL). After 20 h at rt, water (2.0 mL) was added and the mixture was acidified with 1 N aqueous HCl (1.5 mL) and extracted with EtOAc (3×10 mL). The combined extracts were washed with brine (10 mL) then dried ($Na_2SO_4$), filtered and concentrated in vacuo. Purification of the residue by flash column chromatography on silica (EtOAc→10% MeOH/EtOAc, gradient) afforded 11.5 mg (38%) of starting ester 79 and 8.5 mg (29%) of the title compound (80).

Preparation 1

1-(1-(4-Methoxybenzyloxy-hexyl)-4-bromobenzene

Step 1. Pentyl Grignard Addition to 4-Bromobenzaldehyde n-Pentyl magnesium bromide (2.0 M in THF, 27 mL, 54 mmol) was added to a solution of 4-bromobenzaldehyde (5.0 g, 27 mmol) in THF (20 mL) at 0° C. under nitrogen. After 1 h, the reaction was quenched with 3 N HCl and extracted with $Et_2O$ (3×120 mL). Combined extracts were washed with brine (100 mL), dried ($Na_2SO_4$), filtered and concentrated in vacuo. Purification of the residue by flash column chromatography on silica gel (5% EtOAc/Hex) afforded 5.1 g (74%) of 1-(4-bromophenyl)-hexan-1-ol.

Step 2. Protection of the Alcohol as its Mpm Ether

Sodium hydride (60% wt. in oil, 0.95 g, 23.8 mmol) was added to a solution of the alcohol from step 1 (5.11 g, 19.9 mmol) in THF and DMF (2:1, 20 mL) at 0° C. under nitrogen. After 1 h at 0° C., 4-methoxybenzyl chloride (3.23 mL, 23.8 mmol) and the reaction was allowed to warm to rt. The reaction was then heated at 80° C. After 17 h, the reaction was allowed to cool to rt, quenched with saturated aqueous $NH_4Cl$ (100 mL) and extracted with EtOAc (3×100 mL). The combined extracts were washed with brine (100 mL), dried ($Na_2SO_4$), filtered and concentrated in vacuo. Purification of the residue by flash column chromatography on silica gel (2% EtOAc/Hex) afforded 7.02 g (94%) of the title compound.

Preparation 2

Isopropyl 5-chloromethylthiophene-2-carboxylate

Step 1. Preparation of the Bis-Isopropyl Ester

DBU (31.3 mL, 209 mmol) and 2-iodopropane (20.9 mL, 209 mmol) were added to a solution of thiophene-2,5-dicarboxylic acid (6.0 g, 34.9 mmol) in acetone (60 mL) at rt under nitrogen. After 21 h at rt, the reaction was quenched with saturated aqueous $NaHCO_3$ (300 mL) and extracted with EtOAc (3×150 mL). The combined extracts were washed with brine (200 mL), dried ($Na_2SO_4$), filtered and concentrated in vacuo to afford 7.59 g (85%) of the diester.

Step 2. Reduction to the Hydroxymethyl Ester

Sodium borohydride (3.36 g, 88.8 mmol) was added to a solution of the diester (7.59 g, 29.6 mmol) in $CH_2Cl_2$/MeOH (1:1, 100 mL) at 0° C. under nitrogen. The ice bath was removed and the reaction was allowed to stir at rt overnight. After 20.5 h at rt the reaction was concentrated in vacuo then aqueous 0.5 N HCl (100 mL) was added. The mixture was extracted with $CH_2Cl_2$ (3×100 mL). The combined extracts were dried ($Na_2SO_4$), filtered and concentrated in vacuo. Purification of the residue by flash column chromatography on silica (5%→60% EtOAc/Hex, gradient) afforded 738 mg (12%) of the alcohol.

Step 3. Conversion of the Alcohol to the Chloride

Methanesulfonyl chloride (0.67 mL, 8.1 mmol) and triethylamine (1.7 mL, 12.2 mmol) were added sequentially and dropwise to a solution of the alcohol (696 mg, 3.48 mmol) in $CH_2Cl_2$ (4.0 mL) at 0° C. under nitrogen. The ice bath was removed and the reaction was allowed to stir overnight at rt. After 17 h, the reaction was quenched with saturated aqueous $NaHCO_3$ (30 mL) and extracted with $CH_2Cl_2$ (3×50 mL). The combined extracts were dried ($Na_2SO_4$), filtered and concentrated in vacuo. Purification of the residue by flash column chromatography on silica (5% EtOAc/Hex) afforded 664 mg (87%) of the title compound.

Preparation 3

Methyl 5-allylthiophene-2-carboxylate

Step 1. Preparation of the Methyl Ester

Acetyl chloride (6.9 mL, 96.6 mmol) was added to a solution of 5-bromo-2-thiophenecarboxylic acid (4.0 g, 19.3 mmol) in methanol (30 mL) at rt. After 17 h at rt, the reaction was heated at reflux for 1.5 h to drive it to completion. The reaction was then cooled to rt and concentrated in vacuo to remove methanol. Saturated aqueous $NH_4Cl$ (120 mL) was added and the mixture was extracted with $CH_2Cl_2$ (3×100 mL). The combined extracts were dried ($Na_2SO_4$), filtered and concentrated in vacuo to afford 3.57 g (84%) of the desired methyl ester as an off white solid.

Step 2. Allylation of the Bromothiophene

Isopropyl magnesium chloride (2.0 M in $Et_2O$, 8.9 mL, 17.8 mmol) was added to a solution of the bromide from step 1 (3.56 g, 16.1 mmol) in THF (10 mL) at −40° C. under nitrogen. The reaction mixture was stirred at −40° C. for 1 h, then copper (I) cyanide (144 mg, 1.61 mmol) and allyl bromide (3.0 mL, 35.4 mmol) were added sequentially. The reaction mixture was stirred at −40° C. for 1 h then was quenched with saturated aqueous $NH_4Cl$ (100 mL) and extracted with EtOAc (3×100 mL). The combined extracts were washed with brine (100 mL), dried ($Na_2SO_4$), filtered and concentrated in vacuo. Purification of the residue by flash column chromatography on silica gel (5% EtOAc/Hex) afforded 2.45 g (83%) of the title compound as a pale yellow oil that solidified on standing.

Preparation 4

1-(1-(4-Methoxybenzyloxy-heptyl)-4-bromobenzene

Step 1. Hexyl Grignard Addition to 4-Bromobenzaldehyde n-Hexyl magnesium bromide (2.0 M in $Et_2O$, 27 mL, 54 mmol) was added to a solution of 4-bromobenzaldehyde (5.0 g, 27 mmol) in THF (20 mL) at 0° C. under nitrogen. After 1.5 h at 0° C., the reaction was quenched slowly with 3 N HCl (20 mL) and concentrated in vacuo. The residue was diluted with water (30 mL) and extracted with $Et_2O$ (3×150 mL). Combined extracts were dried ($Na_2SO_4$), filtered and concentrated in vacuo. Purification of the residue by flash column chromatography on silica gel (5%→10% EtOAc/Hex) afforded 5.6 g (76%) of 1-(4-bromophenyl)-heptan-1-ol.

Step 2. Protection of the Alcohol as its MPM Ether

Sodium hydride (60% wt. in oil, 0.991 g, 24.8 mmol) was added to a solution of the alcohol from step 1 (5.6 g, 20.6 mmol) in THF and DMF (2:1, 30 mL) at 0° C. under nitrogen. After 5 min at 0° C., the reaction was allowed to warm to rt and 4-methoxybenzyl chloride (3.4 mL, 25.0 mmol) was added. The reaction was then heated at 80° C. After 18 h at 80° C., the reaction was allowed to cool to rt, quenched with saturated aqueous $NH_4Cl$ (50 mL) and concentrated in vacuo. The remainder was extracted with EtOAc (3×100 mL). The combined extracts were washed with water (2×100 mL) and brine (75 mL), then dried ($Na_2SO_4$), filtered and concentrated in vacuo. Purification of the residue by flash column chromatography on silica gel (2% EtOAc/Hex) afforded 7.5 g (93%) of the title compound.

| Example# | Structure | EP2 data | | | EP4 data | | Other Receptors (EC50 in nM) | | | | | |
|---|---|---|---|---|---|---|---|---|---|---|---|---|
| | | flipr EC50 | cAMP EC50 | Ki | Ki pH 6.0 | flipr EC50 | KI | hFP | hEP1 | hEP3A | hTP | hIP | hDP |
| 11 | | >10000 | 517 | NA | | NA | >10000 | NA | NA | NA | NA | NA | NA |
| 12 | | 212 | 8 | 387 | | NA | >10000 | NA | NA | NA | NA | NA | NA |

-continued

| Example# | Structure | EP2 data | | | EP4 data | | Other Receptors (EC50 in nM) | | | | |
|---|---|---|---|---|---|---|---|---|---|---|---|
| | | flipr EC50 | cAMP EC50 | Ki | Ki pH 6.0 | flipr EC50 | KI | hFP | hEP1 | hEP3A | hTP | hIP | hDP |
| 13 | | 20 | 1.5 | 190 | | NA | >10000 | NA | NA | 519 | NA | NA | 5763 |
| 14 | | 426 | 27 | 1639 | | NA | >10000 | NA | NA | NA | NA | NA | NA |

-continued
| Example# | Structure | EP2 data | | | EP4 data | | Other Receptors (EC50 in nM) | | | | |
| --- | --- | --- | --- | --- | --- | --- | --- | --- | --- | --- | --- |
| | | flipr EC50 | cAMP EC50 | Ki | Ki pH 6.0 | flipr EC50 | KI | hFP | hEP1 | hEP3A | hTP | hP | hDP |
| 15 | | 1812 | 312 | 5731 | | >10000 | >10000 | NA | NA | NA | NA | NA | 7560 |
| 16 | 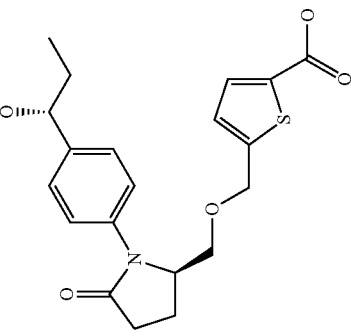 | 226 | 15 | 1382 | | NA | | NA | NA | 1411 | NA | NA | NA |

-continued

| Example# | Structure | EP2 data | | | EP4 data | | Other Receptors (EC50 in nM) | | | | |
|---|---|---|---|---|---|---|---|---|---|---|---|
| | | flipr EC50 | cAMP EC50 | Ki | Ki pH 6.0 | flipr EC50 | KI | hFP | hEP1 | hEP3A | hTP | hIP | hDP |
| 17 | | 5 | 0.55 | 23 | | NA | >10000 | NA | NA | 155 | NA | NA | 1234 |
| 19 | | 16 | 1.6 | 31 | | >10000 | >10000 | NA | NA | 2345 | NA | NA | 7695 |

-continued

| Example# | Structure | EP2 data | | | EP4 data | | Other Receptors (EC50 in nM) | | | | |
| --- | --- | --- | --- | --- | --- | --- | --- | --- | --- | --- | --- |
| | | flipr EC50 | cAMP EC50 | Ki | Ki pH 6.0 | flipr EC50 | KI | hFP | hEP1 | hEP3A | hTP | hIP | hDP |
| 20 | (structure: hexanoyl-phenyl pyrrolidinone with thiophene carboxylate) | 215 | 8 | 163 | | NA | >10000 | NA | NA | NA | NA | NA | NA |
| 23 | (structure: hydroxyhexyl-phenyl pyrrolidinone with thiophene carboxylate; from faster eluting ester) | 62 | 5 | 345 | | >10000 | >10000 | NA | NA | 153 | NA | NA | 7749 |

-continued
| Example# | Structure | EP2 data flipr EC50 | EP2 data cAMP EC50 | EP2 data Ki | Ki pH 6.0 | EP4 data flipr EC50 | EP4 data Ki | Other Receptors (EC50 in nM) hFP | hEP1 | hEP3A | hTP | hIP | hDP |
|---|---|---|---|---|---|---|---|---|---|---|---|---|---|
| 24 | 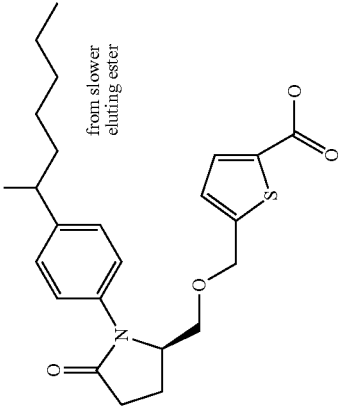 from slower eluting ester | 15 | 1.5 | 116 | | >10000 | 6032 | NA | NA | 1205 | NA | NA | 6800 |
| 27 | 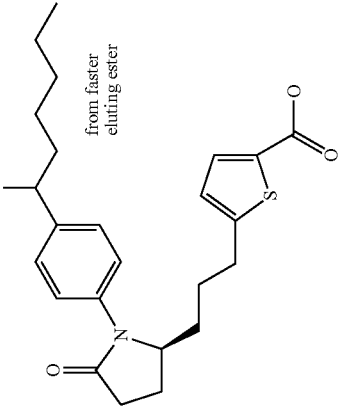 from faster eluting ester | 6 | 0.19 | 21 | | >10000 | >10000 | NA | NA | 12 | NA | NA | 812 |

-continued

| Example# | Structure | EP2 data | | | EP4 data | | Other Receptors (EC50 in nM) | | | | | |
|---|---|---|---|---|---|---|---|---|---|---|---|---|
| | | flipr EC50 | cAMP EC50 | Ki | Ki pH 6.0 | flipr EC50 | KI | hFP | hEP1 | hEP3A | hTP | hIP | hDP |
| 28 | (from slower eluting ester) | 1.6 | 0.15 | 15 | | >10000 | 4849 | NA | NA | 156 | NA | NA | 296 |
| 34 | (from faster eluting ester) | 134 | 7 | 229 | | NA | 3842 | NA | NA | 71 | NA | NA | 6829 |

-continued
| Example# | Structure | EP2 data | | | EP4 data | | Other Receptors (EC50 in nM) | | | | | |
| --- | --- | --- | --- | --- | --- | --- | --- | --- | --- | --- | --- | --- |
| | | flipr EC50 | cAMP EC50 | Ki | Ki pH 6.0 | flipr EC50 | KI | hFP | hEP1 | hEP3A | hTP | hIP | hDP |
| 35 | 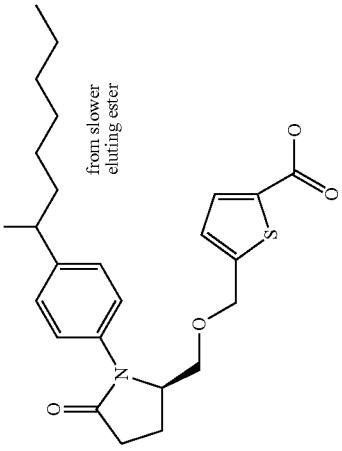 from slower eluting ester | 49 | 4 | 201 | | NA | 3288 | NA | NA | 621 | NA | NA | NA |
| 36 | 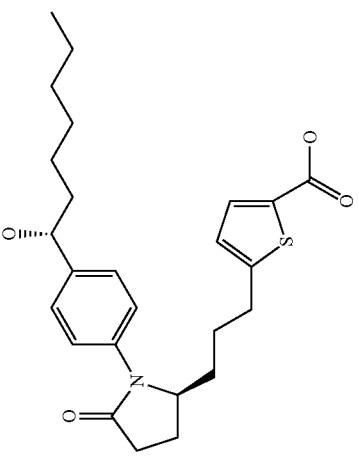 | 30 | 0.9 | 10 | | >10000 | | NA | NA | 47 | NA | NA | 105 |

-continued
| Example # | Structure | EP2 data | | | EP4 data | | Other Receptors (EC50 in nM) | | | | |
|---|---|---|---|---|---|---|---|---|---|---|---|
| | | flipr EC50 | cAMP EC50 | Ki | Ki pH 6.0 | flipr EC50 | KI | hFP | hEP1 | hEP3A | hTP | hIP | hDP |
| 39 | 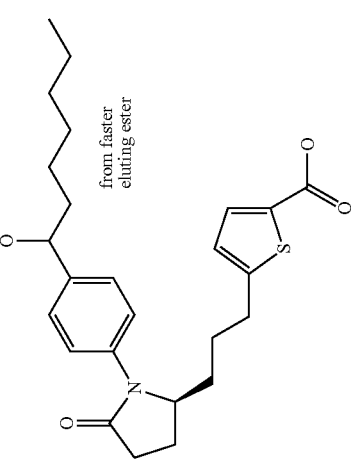 from faster eluting ester | 16 | 1.4 | 12 | | NA | | NA | 6952 | 7 | NA | NA | 37 |
| 40 | 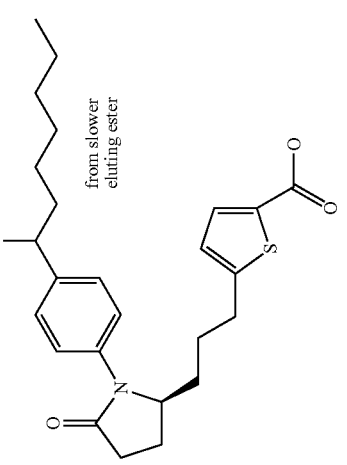 from slower eluting ester | 5 | 0.6 | 8 | | NA | | NA | NA | 33 | NA | >10000 | 106 |

-continued
| Example# | Structure | EP2 data | | | EP4 data | | Other Receptors (EC50 in nM) | | | | |
|---|---|---|---|---|---|---|---|---|---|---|---|
| | | flipr EC50 | cAMP EC50 | Ki | Ki pH 6.0 | flipr EC50 | KI | hFP | hEP1 | hEP3A | hTP | hP | hDP |
| 43 | 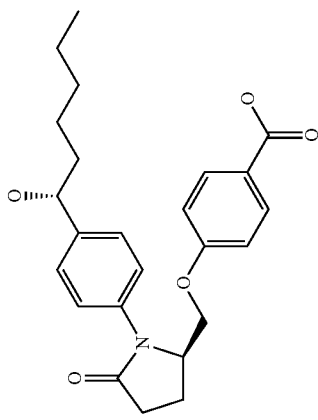 | 7284 | NA | 22726 | | NA | 8752 | NA | NA | NA | NA | NA | NA |

Biological Assay Methods

Binding Data

Ki

Competition binding experiments were performed in a medium containing Hank's balanced salt solution, Hepes 20 mM, pH 7.3, membranes (~60 μg protein) or $2\times10^5$ cells from HEK 293 cells stably expressing human EP2 receptors, [$^3$H] PGE2 (10 nM) and various concentrations of test compounds in a total volume of 300 μl. Reaction mixtures were incubated at 23° C. for 60 min, and were filtered over Whatman GF/B filters under vacuum. Filters were washed three times with 5 ml ice-cold buffer containing 50 mM Tris/HCl (pH 7.3). Non-specific binding was estimated in the presence of excess unlabeled PGE2 (10 μM). Binding data fitted to the binding model for a single class of binding sites, using nonlinear regression analysis. $IC_{50}$ values thus obtained were converted to Ki using the equation of $Ki=(IC_{50}/(1+[L]/K_D)$ where [L] represents PGE2 concentration (10 nM) and $K_D$ the dissociation constant for [$^3$H]PGE2 at human EP2 receptors (40 nM).

Radioligand Binding

Cells Stably Expressing $EP_1$, $EP_2$, $EP_4$ and FP Receptors

HEK-293 cells stably expressing the human or feline FP receptor, or $EP_1$, $EP_2$, or $EP_4$ receptors were washed with TME buffer, scraped from the bottom of the flasks, and homogenized for 30 sec using a Brinkman PT 10/35 polytron. TME buffer was added to achieve a final 40 ml volume in the centrifuge tubes (the composition of TME is 100 mM TRIS base, 20 mM $MgCl_2$, 2M EDTA; 10N HCl is added to achieve a pH of 7.4).

The cell homogenate was centrifuged at 19000 r.p.m. for 20 min at 4° C. using a Beckman Ti-60 rotor. The resultant pellet was resuspended in TME buffer to give a final 1 mg/ml protein concentration, as determined by Biorad assay. Radioligand binding competition assays vs. [$^3$H-]17-phenyl $PGF_{2\alpha}$ (5 nM) were performed in a 1001 volume for 60 min. Binding reactions were started by adding plasma membrane fraction. The reaction was terminated by the addition of 4 ml ice-cold TRIS-HCl buffer and rapid filtration through glass fiber GF/B filters using a Brandel cell harvester. The filters were washed 3 times with ice-cold buffer and oven dried for one hour.

[$^3$H-] $PGE_2$ (specific activity 180 Ci mmol) was used as the radioligand for EP receptors. [$^3$H] 17-phenyl $PGF_2$, was employed for FP receptor binding studies. Binding studies employing $EP_1$, $EP_2$, $EP_4$ and FP receptors were performed in duplicate in at least three separate experiments. A 200 μl assay volume was used. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Competition studies were performed using a final concentration of 5 nM [$^3$H]-$PGE_2$, or 5 nM [$^3$H] 17-phenyl $PGF_2$, and non-specific binding determined with $10^{-5}$M of unlabeled $PGE_2$, or 17-phenyl $PGF_{2\alpha}$, according to receptor subtype studied.

Methods for FLIPR™ Studies (a) Cell Culture

HEK-293(EBNA) cells, stably expressing one type or subtype of recombinant human prostaglandin receptors (prostaglandin receptors expressed: hDP/Gqs5; $hEP_1$; $hEP_2$/Gqs5; $hEP_{3A}$/Gqi5; $hEP_4$/Gqs5; hFP; hIP; hTP), were cultured in 100 mm culture dishes in high-glucose DMEM medium containing 10% fetal bovine serum, 2 mM 1-glutamine, 250 μg/ml geneticin (G418) and 200 μg/ml hygromycin B as selection markers, and 100 units/ml penicillin G, 100 μg/ml streptomycin and 0.25 μg/ml amphotericin B.

(b) Calcium Signal Studies on The FLIPR™

Cells were seeded at a density of $5\times10^4$ cells per well in Biocoat® Poly-D-lysine-coated black-wall, clear-bottom 96-well plates (Becton-Dickinson) and allowed to attach overnight in an incubator at 37° C. Cells were then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 μM at a final concentration of 2 μM, plates were washed four times with HBSS-HEPES buffer to remove excess dye leaving 100 μl in each well. Plates were re-equilibrated to 37° C. for a few minutes.

Cells were excited with an Argon laser at 488 nm, and emission was measured through a 510-570 nm bandwidth emission filter (FLIPR™, Molecular Devices, Sunnyvale, Calif.). Drug solution was added in a 50 μl volume to each well to give the desired final concentration. The peak increase in fluorescence intensity was recorded for each well. On each plate, four wells each served as negative (HBSS-HEPES buffer) and positive controls (standard agonists: BW245C (hDP); $PGE_2$ ($hEP_1$; $hEP_2$/Gqs5; $hEP_{3A}$/Gqi5; $hEP_4$/Gqs5); $PGF_{2\alpha}$ (hFP); carbacyclin (hIP); U-46619 (hTP), depending on receptor). The peak fluorescence change in each drug-containing well was then expressed relative to the controls.

Compounds were tested in a high-throughput (HTS) or concentration-response (CoRe) format. In the HTS format, forty-four compounds per plate were examined in duplicates at a concentration of $10^{-5}$ M. To generate concentration-response curves, four compounds per plate were tested in duplicates in a concentration range between $10^{-5}$ and $10^{-11}$ M. The duplicate values were averaged. In either, HTS or CoRe format each compound was tested on at least 3 separate plates using cells from different passages to give an n>3.

Intraocular Pressure (IOP)

Intraocular pressure studies in dogs involve pneumatonometry performed on conscious Beagle dogs of both sexes (10-15 kg). The animals remain conscious throughout the study and are gently restrained by hand. Drugs are administered topically to one eye as a 25 μL volume drop, the other eye receives 25 μL vehicle (0.1% polysorbate 80:10 mM TRIS) as a control. Proparacaine (0.1%) is used for corneal anesthesia during tonometry. Intraocular pressure is determined just before drug administration and at 2, 4 and 6 hr thereafter on each day of the 5 day study. Drug is administered immediately after the first IOP reading.

The results of the binding and activity studies, presented in Table 1 below, demonstrate that the compounds disclosed herein are selective prostaglandin $EP_2$ agonists, and are thus useful for the treatment of glaucoma, ocular hypertension, inflammatory bowel disease, and the other diseases or conditions disclosed herein.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof, rather, the ambit of the present invention is to be governed only by the lawful construction of the appended claims.

What is claimed is:
1. A compound according to a formula selected from
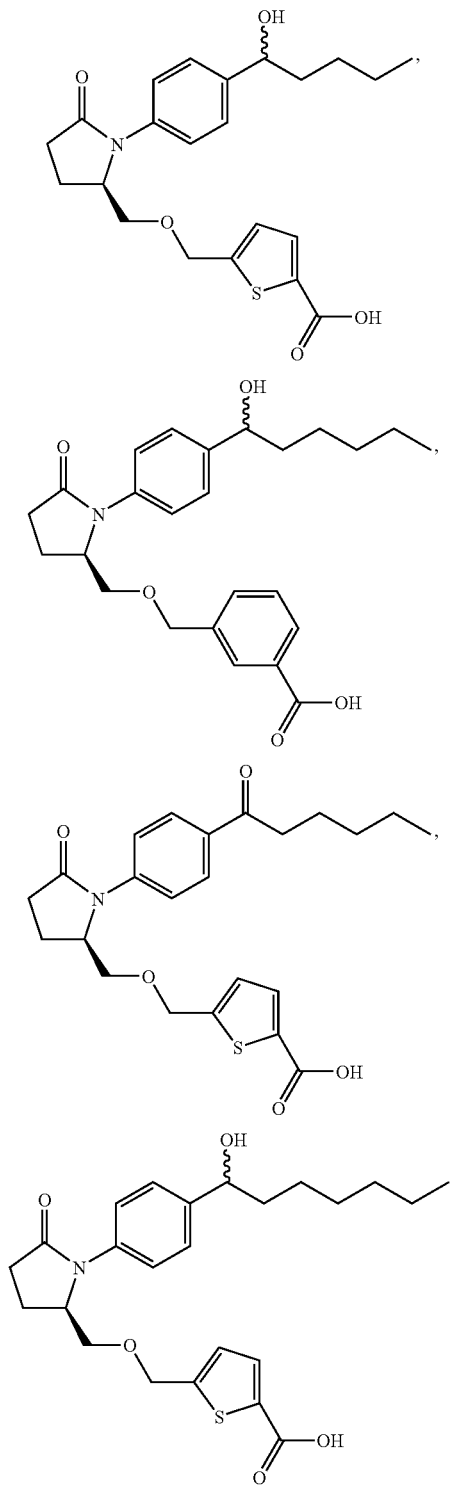
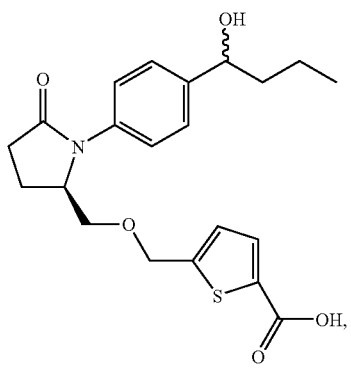
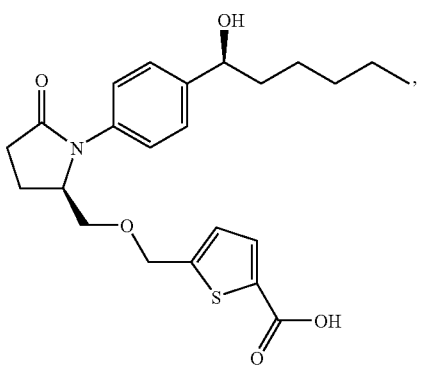
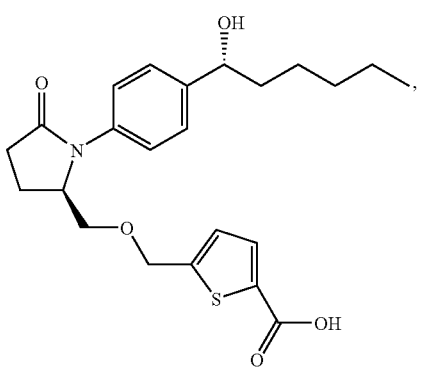
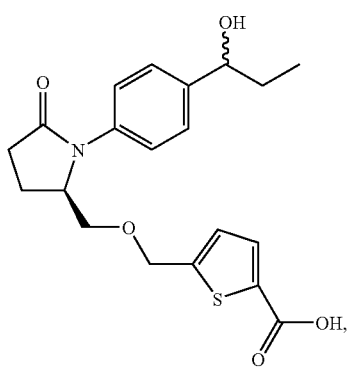

61
-continued
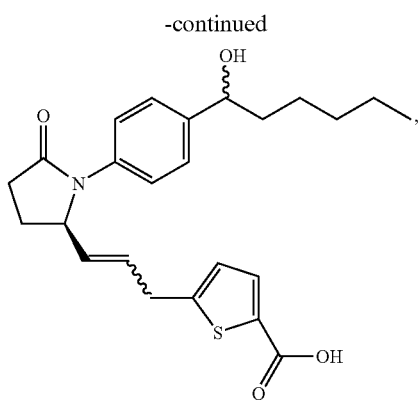
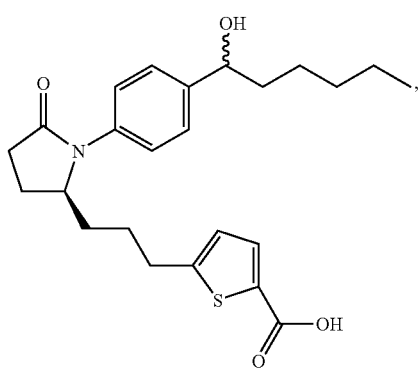
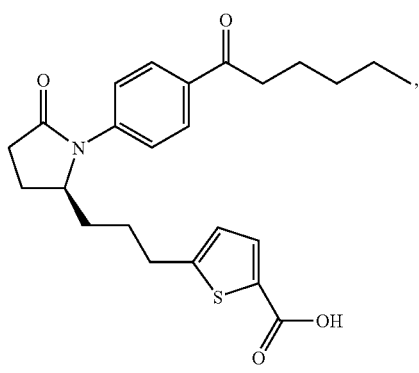
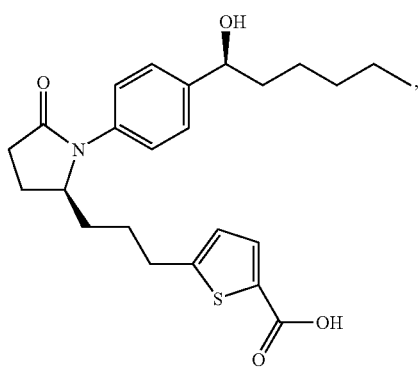
62
-continued
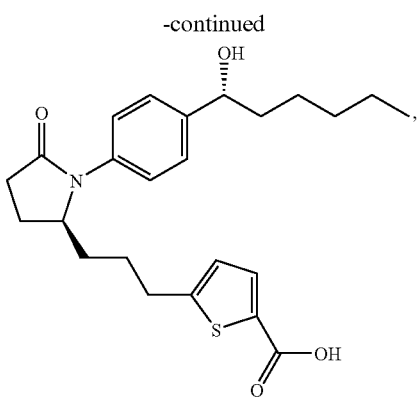
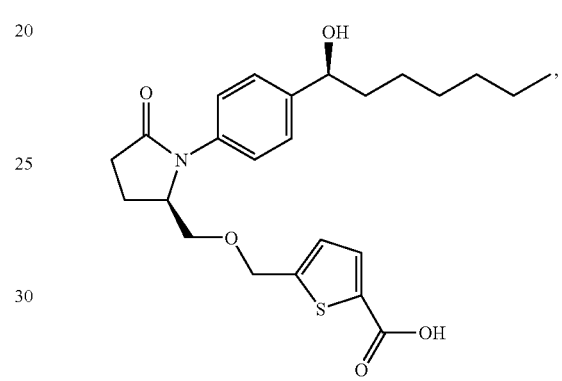
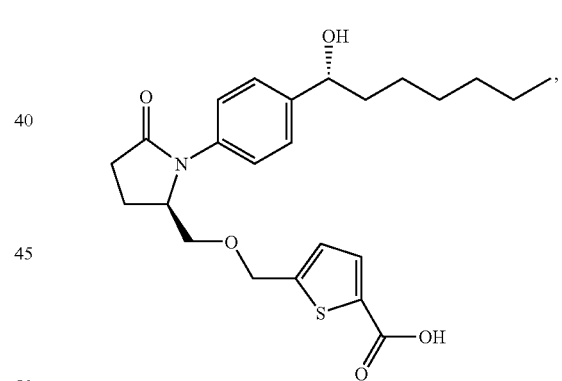
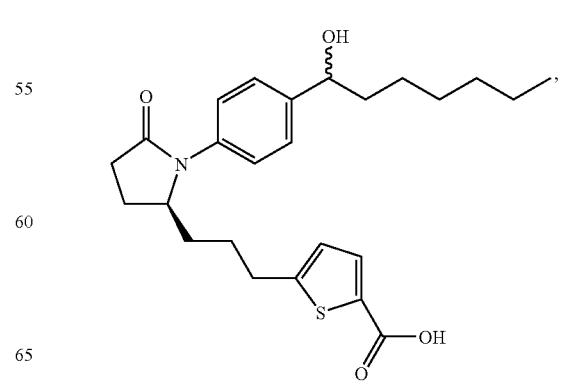

-continued

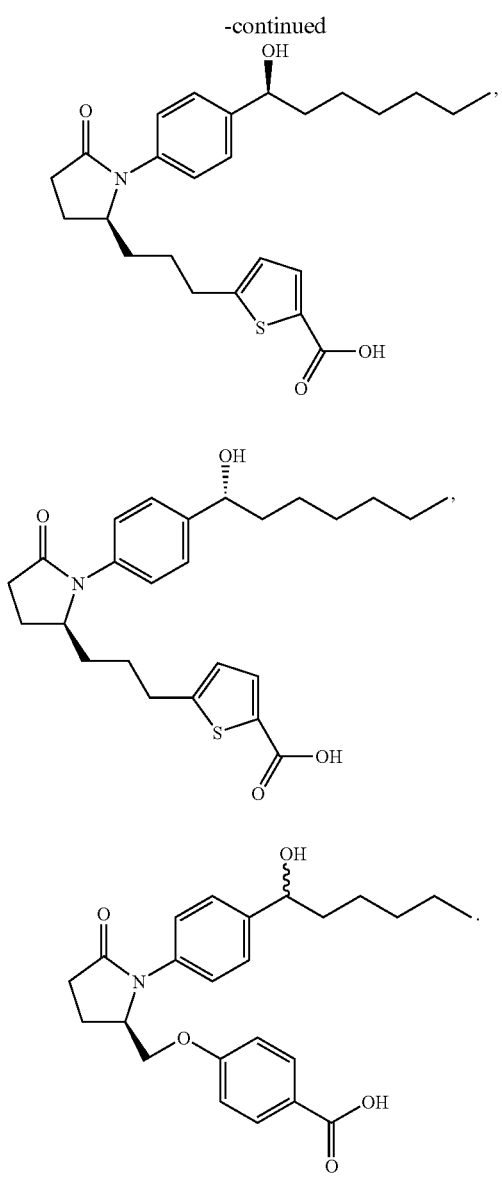

2. The compound of claim 1 according to the formula

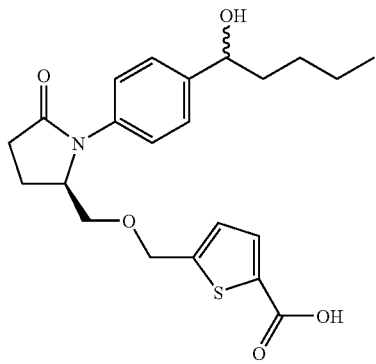

or a pharmaceutically acceptable salt thereof.

3. The compound of claim 1 according to the formula

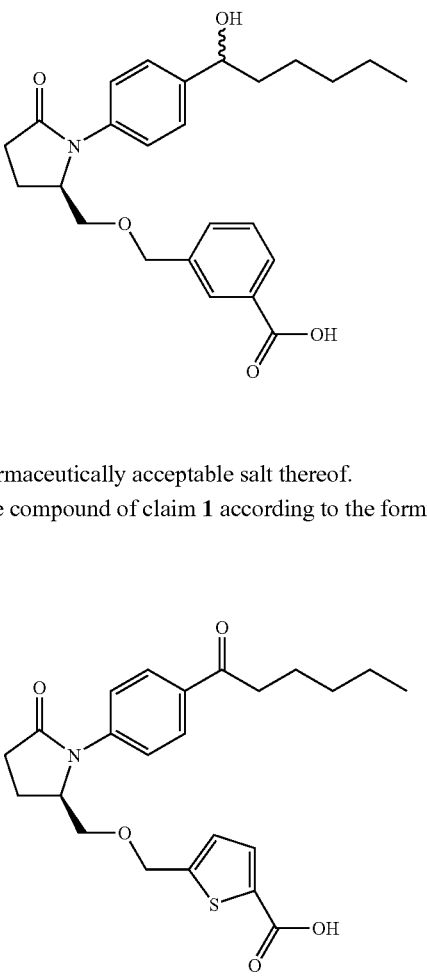

or a pharmaceutically acceptable salt thereof.

4. The compound of claim 1 according to the formula

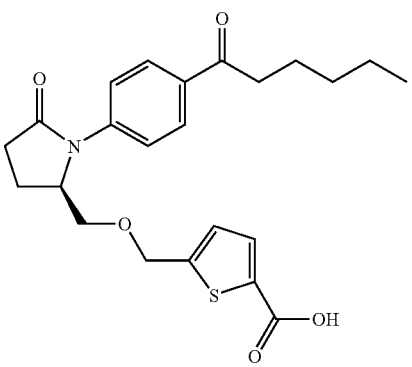

or a pharmaceutically acceptable salt thereof.

5. The compound of claim 1 according to the formula

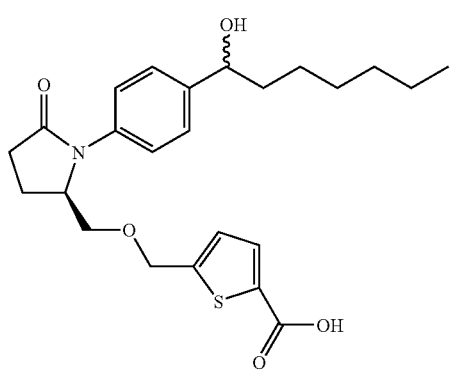

or a pharmaceutically acceptable salt thereof.

6. The compound of claim 1 according to the formula

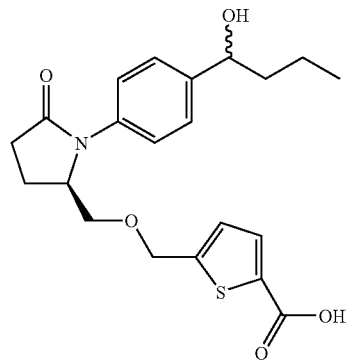

or a pharmaceutically acceptable salt thereof.

7. The compound of claim 1 according to the formula

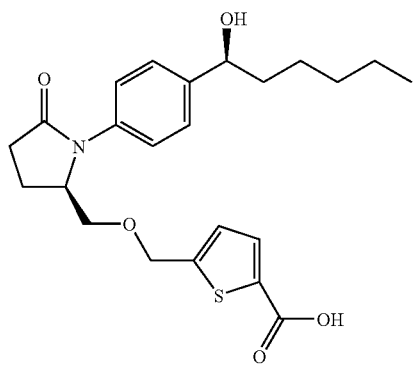

or a pharmaceutically acceptable salt thereof.

8. The compound of claim 1 according to the formula

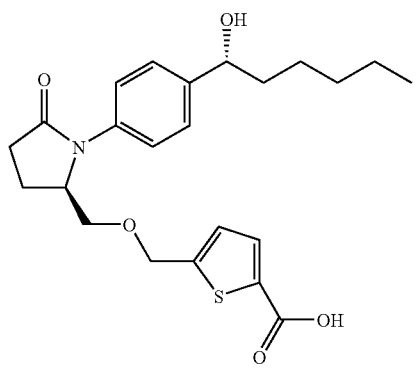

or a pharmaceutically acceptable salt thereof.

9. The compound of claim 1 according t the formula

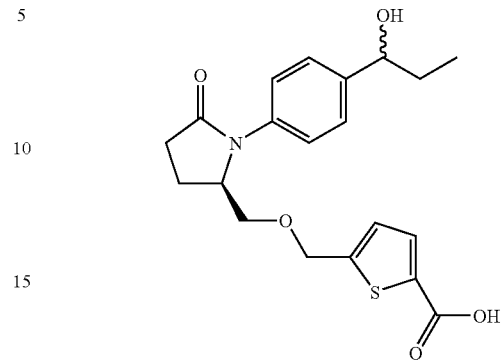

or a pharmaceutically acceptable salt thereof.

10. The compound of claim 1 according to the formula

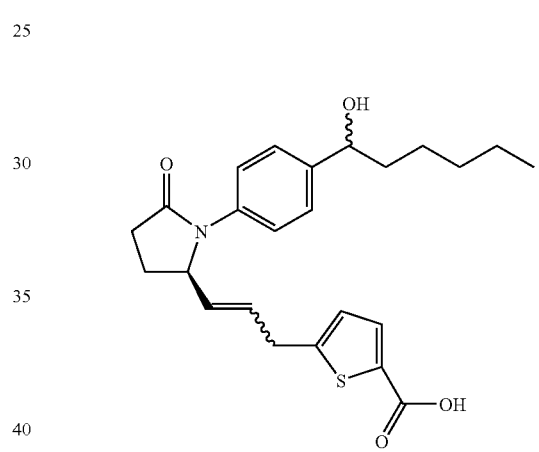

or a pharmaceutically acceptable salt thereof.

11. The compound of claim 1 according to the formula

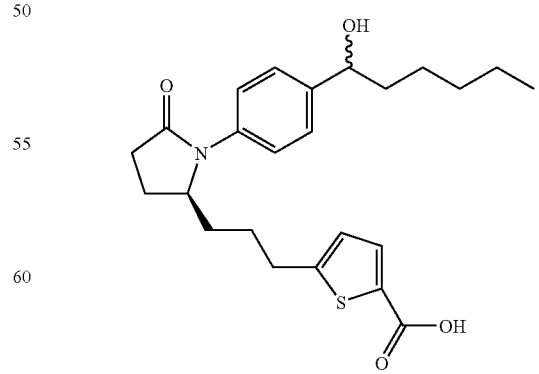

or a pharmaceutically acceptable salt thereof.

12. The compound of claim 1 according to the formula

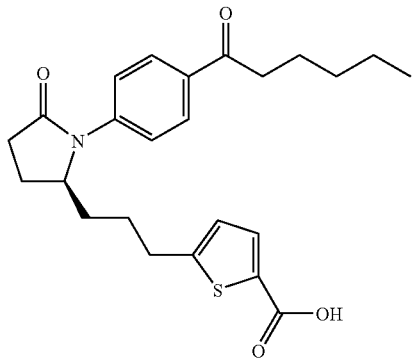

or a pharmaceutically acceptable salt thereof.

13. The compound of claim 1 according to the formula

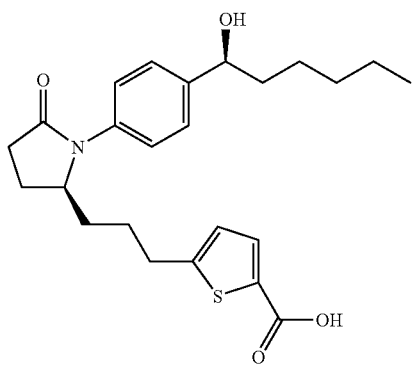

or a pharmaceutically acceptable salt thereof.

14. The compound of claim 1 according to the formula

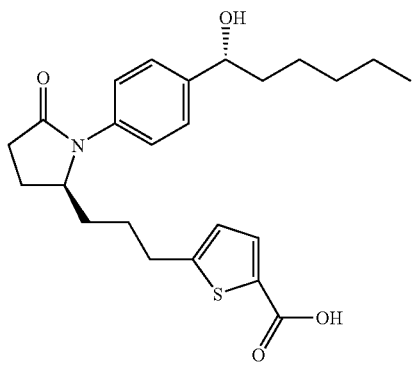

or a pharmaceutically acceptable salt thereof.

15. The compound of claim 1 according to the formula

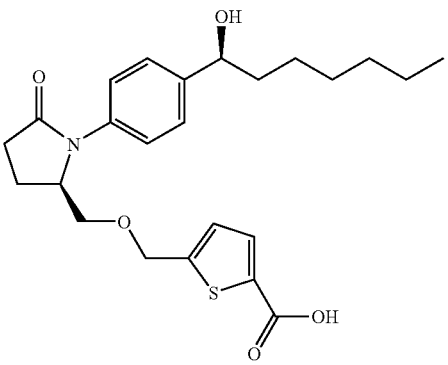

or a pharmaceutically acceptable salt thereof.

16. The compound of claim 1 according to the formula

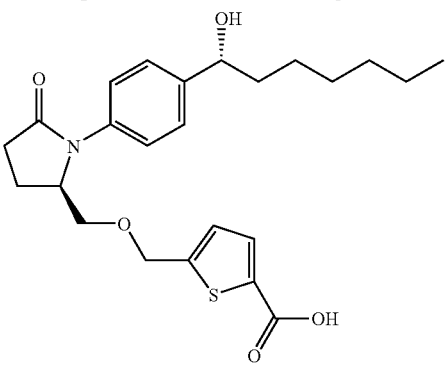

or a pharmaceutically acceptable salt thereof.

17. The compound of claim 1 according to the formula

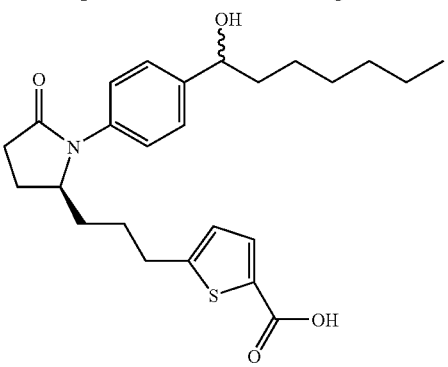

or a pharmaceutically acceptable salt thereof.

18. The compound of claim 1 according to the formula

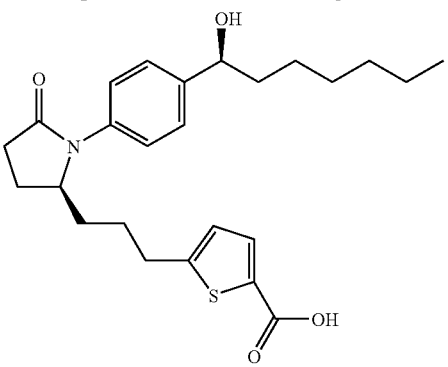

or a pharmaceutically acceptable salt thereof.

19. compound of claim 1 according to the formula
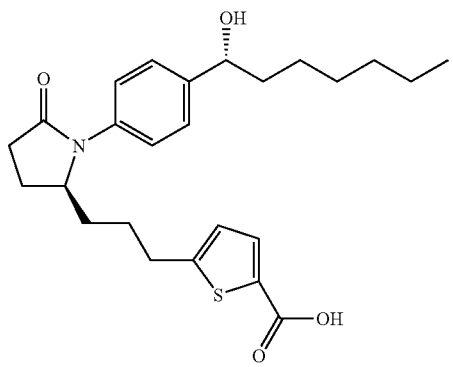
or a pharmaceutically acceptable salt thereof.
20. The compound of claim 1 according to the formula
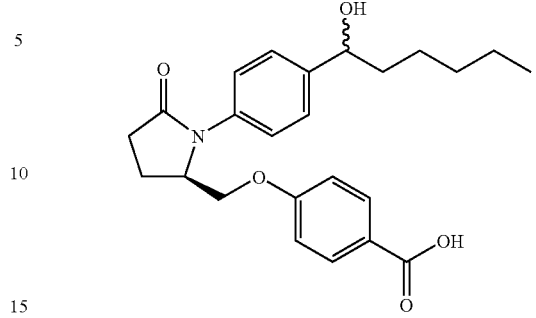
or a pharmaceutically acceptable salt thereof.
* * * * *